US008691535B2

(12) United States Patent
Aehle et al.

(10) Patent No.: US 8,691,535 B2
(45) Date of Patent: Apr. 8, 2014

(54) SUCROSE MUTASE WITH IMPROVED PRODUCT SPECIFICITY

(75) Inventors: Wolfgang Aehle, Zwingenberg (DE); Juergen Eck, Bensheim (DE); Karsten Harms, Worms (DE); Michael Klingeberg, Grünstaadt (DE); Stefan Pelzer, Pfungstadt (DE); Wolfgang Wach, Worms (DE)

(73) Assignee: Südzucker Aktiengesellschaft Mannheim/Ochsenfurt, Mannheim (DE)

( * ) Notice: Subject to any disclaimer, the term of this patent is extended or adjusted under 35 U.S.C. 154(b) by 0 days.

(21) Appl. No.: 13/518,849

(22) PCT Filed: Dec. 18, 2010

(86) PCT No.: PCT/EP2010/007767
§ 371 (c)(1),
(2), (4) Date: Jun. 22, 2012

(87) PCT Pub. No.: WO2011/076370
PCT Pub. Date: Jun. 30, 2011

(65) Prior Publication Data
US 2012/0315673 A1 Dec. 13, 2012

(30) Foreign Application Priority Data
Dec. 23, 2009 (DE) .......................... 10 2009 060 935

(51) Int. Cl.
C12P 19/24 (2006.01)
C12N 15/64 (2006.01)
C12P 21/04 (2006.01)
C12P 21/06 (2006.01)

(52) U.S. Cl.
USPC ........... 435/94; 435/69.1; 435/71.1; 435/91.4

(58) Field of Classification Search
None
See application file for complete search history.

(56) References Cited

U.S. PATENT DOCUMENTS 4,857,461 A 8/1989 Egerer et al.
5,786,140 A 7/1998 Mattes et al.
5,985,622 A * 11/1999 Mattes et al. ................. 435/100

FOREIGN PATENT DOCUMENTS

DE 35 28 752 A1 10/1986
DE 100 45 182 A1 8/2001
WO WO 2004/005504 A1 1/2004

OTHER PUBLICATIONS

Copy of International Search Report from PCT/EP2010/007767, dated May 9, 2011 (English Translation copy).
Uniprot Database Accession No. Q9A164; ID No. Q9A164_ERWRD; "Sucrose isomerase"; Jun. 1, 2001 (1 page).
Uniprot Database Accession No. Q6XNK5; Id No. Q6XNK5; "Sucrose isomerase"; Jul. 5, 2004 (1 page).
Uniprot Database Accession No. Q9K8U9; ID No. O16G_BACHD; "oligo-1,6-glucosidase"; Oct. 1, 2000 (1 page).
GenBank Accession No. AY223549; "Pantoea dispersa sucrose isomerase gene, complete cds", Mar. 4, 2005 (1 page).
GenBank Accession No. AY227804; "Raoultella planticola sucrose isomerase gene, complete cds", Mar. 4, 2005 (1 page).
GenBank Accession No. AF279281; "Erwinia rhapontici sucrose isomerase (pal1) gene, complete cds", Apr. 3, 2001 (2 page).
Clustal multiple sequence alignment retrieved from the internet at www.ebi.ac.uk/Tools/services/rest/clustalw2/result/clustalw2-I20101210-122909-0678-2828982/ain . . . on Dec. 12, 2010 (2 pages).
Lee et al.; "Isomaltose production by modification of the fructose-binding site on the basis of the predicted structure of sucrose isomerase from *Protoaminobacter rubrum*"; *Applied and Environmental*; 74(16):5183-5194 (2008).
Wu et al.; "Characterization of the highly efficient su-crose isomerase from *Pantoea dispersa*UQ68J and cloning of the sucrose isomerase gene"; *Applied and Environmental Microbiology*; 71(3):1581-1590.
Copy of an Office Action from CN Appl. No. 201080058570.6, dated Apr. 1, 2013 (17 pages).
Ravaud et al.; "Overexpression, purification, crystallization and preliminary diffraction studies of the *Protaminobacter rubrum*sucrose isomerase SmuA"; *Acta Cryst.*; F62:74-76 (2006).
Ravaud et al.; "Structural determinants of product specificity of sucrose isomerases"; *FEBS Letters*; 583:1964-1968 (2008).

* cited by examiner

*Primary Examiner* — John S Brusca
*Assistant Examiner* — Gerard Lacourciere
(74) *Attorney, Agent, or Firm* — Kilpatrick Townsend & Stockton LLP

(57) ABSTRACT

For the biotechnological production of isomaltulose and compositions containing isomaltulose from saccharose the invention provides improved means, particularly a sucrose mutase with improved product specificity as well as microbial cells containing the improved sucrose mutase.

20 Claims, 3 Drawing Sheets

SEQUENCE LISTING

<160> NUMBER OF SEQ ID NOS: 4

<210> SEQ ID NO 1
<211> LENGTH: 573
<212> TYPE: PRT
<213> ORGANISM: Protaminobacter rubrum

<400> SEQUENCE: 1

```
Thr Gln Gln Pro Leu Leu Asn Glu Lys Ser Ile Glu Gln Ser Lys Thr
1               5                   10                  15

Ile Pro Lys Trp Trp Lys Glu Ala Val Phe Tyr Gln Val Tyr Pro Arg
            20                  25                  30

Ser Phe Lys Asp Thr Asn Gly Asp Gly Ile Gly Asp Ile Asn Gly Ile
        35                  40                  45

Ile Glu Lys Leu Asp Tyr Leu Lys Ala Leu Gly Ile Asp Ala Ile Trp
    50                  55                  60

Ile Asn Pro His Tyr Asp Ser Pro Asn Thr Asp Asn Gly Tyr Asp Ile
65                  70                  75                  80

Arg Asp Tyr Arg Lys Ile Met Lys Glu Tyr Gly Thr Met Glu Asp Phe
                85                  90                  95

Asp Arg Leu Ile Ser Glu Met Lys Lys Arg Asn Met Arg Leu Met Ile
            100                 105                 110

Asp Val Val Ile Asn His Thr Ser Asp Gln Asn Glu Trp Phe Val Lys
        115                 120                 125

Ser Lys Ser Ser Lys Asp Asn Pro Tyr Arg Gly Tyr Tyr Phe Trp Lys
    130                 135                 140

Asp Ala Lys Glu Gly Gln Ala Pro Asn Asn Tyr Pro Ser Phe Phe Gly
145                 150                 155                 160

Gly Ser Ala Trp Gln Lys Asp Glu Lys Thr Asn Gln Tyr Tyr Leu His
                165                 170                 175

Tyr Phe Ala Lys Gln Gln Pro Asp Leu Asn Trp Asp Asn Pro Lys Val
            180                 185                 190

Arg Gln Asp Leu Tyr Ala Met Leu Arg Phe Trp Leu Asp Lys Gly Val
        195                 200                 205

Ser Gly Leu Arg Phe Asp Thr Val Ala Thr Tyr Ser Lys Ile Pro Asp
    210                 215                 220

Phe Pro Asn Leu Thr Gln Gln Gln Leu Lys Asn Phe Ala Ala Glu Tyr
225                 230                 235                 240

Thr Lys Gly Pro Asn Ile His Arg Tyr Val Asn Glu Met Asn Lys Glu
                245                 250                 255

Val Leu Ser His Tyr Asp Ile Ala Thr Ala Gly Glu Ile Phe Gly Val
            260                 265                 270

Pro Leu Asp Gln Ser Ile Lys Phe Phe Asp Arg Arg Arg Asp Glu Leu
        275                 280                 285

Asn Ile Ala Phe Thr Phe Asp Leu Ile Arg Leu Asp Arg Asp Ser Asp
    290                 295                 300

Gln Arg Trp Arg Arg Lys Asp Trp Lys Leu Ser Gln Phe Arg Gln Ile
305                 310                 315                 320

Ile Asp Asn Val Asp Arg Thr Ala Gly Glu Tyr Gly Trp Asn Ala Phe
                325                 330                 335

Phe Leu Asp Asn His Asp Asn Pro Arg Ala Val Ser His Phe Gly Asp
            340                 345                 350

Asp Arg Pro Gln Trp Arg Glu Pro Ser Ala Lys Ala Leu Ala Thr Leu
        355                 360                 365
```

```
Thr Leu Thr Gln Arg Ala Thr Pro Phe Ile Tyr Gln Gly Ser Glu Leu
    370                 375                 380
Gly Met Thr Asn Tyr Pro Phe Lys Ala Ile Asp Glu Phe Asp Asp Ile
385                 390                 395                 400
Glu Val Lys Gly Phe Trp His Asp Tyr Val Glu Thr Gly Lys Val Lys
                405                 410                 415
Ala Asp Glu Phe Leu Gln Asn Val Arg Leu Thr Ser Arg Asp Asn Ser
            420                 425                 430
Arg Thr Pro Phe Gln Trp Asp Gly Ser Lys Asn Ala Gly Phe Thr Ser
        435                 440                 445
Gly Lys Pro Trp Phe Lys Val Asn Pro Asn Tyr Gln Glu Ile Asn Ala
    450                 455                 460
Val Ser Gln Val Thr Gln Pro Asp Ser Val Phe Asn Tyr Tyr Arg Gln
465                 470                 475                 480
Leu Ile Lys Ile Arg His Asp Ile Pro Ala Leu Thr Tyr Gly Thr Tyr
                485                 490                 495
Thr Asp Leu Asp Pro Ala Asn Asp Ser Val Tyr Ala Tyr Thr Arg Ser
            500                 505                 510
Leu Gly Ala Glu Lys Tyr Leu Val Val Asn Phe Lys Glu Gln Met
        515                 520                 525
Met Arg Tyr Lys Leu Pro Asp Asn Leu Ser Ile Glu Lys Val Ile Ile
    530                 535                 540
Asp Ser Asn Ser Lys Asn Val Val Lys Asn Asp Ser Leu Leu Glu
545                 550                 555                 560
Leu Lys Pro Trp Gln Ser Gly Val Tyr Lys Leu Asn Gln
                565                 570

<210> SEQ ID NO 2
<211> LENGTH: 1942
<212> TYPE: DNA
<213> ORGANISM: Protaminobacter rubrum

<400> SEQUENCE: 2
cccgggatcg cattcatgtt ttctccttcg gtgaagtggt ctactttat ggcgatttgt      60
atacattaaa gtgatcaagg aaaaaatagc cagaggaata gccaaataaa tttcaggttt     120
tacagtgcgg taacctcttt tgttgcgcg gttatcagga ttcatttagg gataaagagg      180
tcttcaagtg atctacaaaa cgcttgctga acgtctgaga atacgtatca attctgctga     240
ttttgctatc ggcgatgctt tacccagtga gaaacgtctg gctgccgaat tttctgtatc     300
gaggatgaca ctccgcaaag cggtaaattt actgattgaa tgggggctgg tacgtcgctg     360
tcacggcagc ggaaccttcg tcgcgcagaa agatctccaa catgaaactc gtgggctgat     420
ggggttttca gaactgatga agaactgggg ccgccccacg gtgagcgagg tgctggagtt     480
tcgaatgatg ggagccccc cagccatcgc cagccagctg cgaatcaagg ccgatgaacg     540
catttactat tcgcgtcgcg taaggtttgt ggaagggaag cctgtggtgc tggaagatag     600
ttacatgcct ggcaggttat ttggcaacct ttcagtcgca catctggagg ttcaaagtt     660
ttcgtatata gaagacgaat gccatatcaa tatcgcaggg aattacgaaa gcttcagccc     720
gatcttggca gacagcacga tcggcgcgct actgcacgtt gccgaaggca cgccgctgct     780
gcgcctgaca tcgctttctt acagtgatac cggcgactat atcaactatt cggtgatatt     840
cagaaatgcc aatgaatacc acgtggacta ccatttgaag aggaataaat agcgggcgaa    900
ggggagctac attcctacta tatagcaatt ctgttgccta gtgtaatgcg agttgcccgc    960
```

-continued

```
cggataaacc aataaccgca ttctccgcag ggggccgaat tgtgcttttg ccaattgccc    1020
tgattaatca ttagcgttat agtcagaatg cttattctca gggcggggtg caagtccca    1080 ccggcggtaa atcaccttct acggtgaaag cccgcgagcg ctcagccagt ctcttgtagt    1140
ttggttagag gtcagcagat ccggtgtaat tccggggccg acggttatag tccggatggg    1200
agagagtaac ggtatctgcc gggcttgcgc ccgcttgcgt tattttttta gaaacaggag    1260
agtattgtaa tgcattttgt ttaaactaaa tcaataaatc tcatagtcac gccaaataat    1320
gtaaatatat tgaaactatt aaaaccggca ttttatgccg gttttttag cgcaaaatag    1380 ggctggcaaa gataaagcag gaggctacca ccgtgagcta tatgcttttt taaaaggcaa    1440
gattctccat cgaggctctg ccgtcacccg aacgcgataa accgcgttta tcctcagatg    1500
cctggccgtt gcgcgcaaac gaagaccggg gtttgagggc ttgtggggca acgccggcga    1560
gccagtcagc ttctcgtggg tgcgagcaca ttgctaatga acaatctcgc ttcaaatgtt    1620
atcgtgagaa tgaagtgttg cagtggcgcc gccggggttt gcgctcgatt caggtctgat    1680
tcacataaca aggtcacatg gaaatgaaag tgttattcat cgcttcgcta ggcgctttat    1740
cgttaatgca agcatcattc tccttcgcgg ataatgccaa tgggaaaaac atctattcac    1800
agagatgtac tatgtgccac ggaaccgatc tcaaaggcac ggggccattg gctgataaaa    1860
ccaacccgcc gacacctgat ctgacaaccc ccgctttcaa agcacgcctc aatgattatc    1920
cgggcgttat tgtatcctgc ag                                             1942

<210> SEQ ID NO 3
<211> LENGTH: 1803
<212> TYPE: DNA
<213> ORGANISM: Protaminobacter rubrum

<400> SEQUENCE: 3
atgccccgtc aaggattgaa aactgcacta gcgattttc taaccacatc attatgcatc      60
tcatgccagc aagccttcgg tacgcaacaa cccttgctta acgaaagag tatcgaacag     120 tcgaaaacca tacctaaatg gtggaaggag gctgttttt atcaggtgta ccgcgctcc     180 tttaaagaca ccaacggaga tggcatcggg gatattaacg gcatcataga aaaattagac    240
tatctaaaag ccttggggat tgatgccatt tggatcaacc cacattatga ttctccgaac    300
acggataatg gttacgatat acgtgattat cgaaaaatca tgaaagaata tggcacgatg    360 gaggatttg accgcctgat ttctgaaatg aaaaaacgga atatgcggtt gatgattgat    420
gtggtcatca accacaccag cgatcaaaac gaatggtttg ttaaaagtaa aagcagtaag    480
gataatcctt atcgcggcta ttatttctgg aaagatgcta agaagggca ggcgcctaat    540 aattaccctt cattctttgg tggctcggcg tggcaaaaag atgaaaagac caatcaatac    600
tacctgcact attttgctaa caacagcct gacctaaact gggataatcc caagtccgt    660 caagatcttt atgcaatgtt acgtttctgg ttagataaag gcgtgtctgg tttacgtttt    720
gatacggtag cgacctactc aaaaattccg gatttcccaa atctcacccca caacagctg    780 aagaattttg cagcggagta taccaagggc cctaatattc atcgttacgt caatgaaatg    840
aataaagagg tcttgtctca ttacgacatt gcgactgccg gtgaaatctt tggcgtaccc    900
ttggatcaat cgataaagtt cttcgatcgc cgccgtgatg agctgaacat tgcatttacc    960
tttgacttaa tcagactcga tcgatattct gatcaaagat ggcgtcgaaa agattggaaa    1020
ttgtcgcaat tccggcagat catcgataac gttaccgta ctgcaggaga atatggttgg    1080
aatgccttct tcttggataa ccacgacaat ccgcgcgctg tctcgcactt tggcgatgat    1140
```

-continued

```
cgcccacaat ggcgtgagcc atcggctaaa gcgcttgcaa ccttgacgct gactcaacga    1200
gcaacacctt ttatttatca aggttcagaa ttgggcatga ccaattaccc gtttaaagct    1260
attgatgaat tcgatgatat tgaggtgaaa ggttttttggc atgactacgt tgagacagga    1320
aaggtcaaag ccgacgagtt cttgcaaaat gtacgcctga cgagcaggga taacagccgg    1380
acgccgttcc aatgggatgg gagcaaaaat gcaggattca cgagcggaaa accttggttc    1440
aaggtcaacc caaactacca ggaaatcaat gcagtaagtc aagtcacaca cccgactca    1500
gtatttaact attatcgtca gttgatcaag ataaggcatg acatcccggc actgacctat    1560
ggtacataca ccgatttgga tcctgcaaat gattcggtct acgcctatac acgcagcctt    1620
ggggcggaaa aatatcttgt tgttgttaac ttcaaggagc aaatgatgag atataaatta    1680
ccggataatt tatccattga gaaagtgatt atagacagca cagcaaaaa cgtggtgaaa    1740
aagaatgatt cattactcga gctaaaacca tggcagtcag gggtttataa actaaatcaa    1800
taa                                                                   1803

<210> SEQ ID NO 4
<211> LENGTH: 1803
<212> TYPE: DNA
<213> ORGANISM: Protaminobacter rubrum

<400> SEQUENCE: 4
atgccccgtc aaggattgaa aactgcacta gcgatttttc taaccacatc attatgcatc     60
tcatgccagc aagccttcgg tacgcaacaa cccttgctta cgaaaagag tatcgaacag    120
tcgaaaacca tacctaaatg gtggaaggag gctgttttt atcaggtgta ccgcgctcc    180
tttaaagaca ccaacggaga tggcatcggg gatattaacg gcatcataga aaaattagac    240
tatctaaaag ccttggggat tgatgccatt tggatcaacc cacattatga ttctccgaac    300
acggataatg gttacgatat acgtgattat cgaaaaatca tgaaagaata tggcacgatg    360
gaggattttg accgcctgat ttctgaaatg aaaaaacgga atatgcggtt gatgattgat    420
gtggtcatca accacaccag cgatcaaaac gaatggtttg ttaaaagtaa agcagtaag    480
gataatcctt atcgcggcta ttatttctgg aaagatgcta agaagggca ggcgcctaat    540
aattacccctt cattctttgg tggctcggcg tggcaaaaag atgaaaagac caatcaatac    600
tacctgcact attttgctaa caacagcct gacctaaact gggataatcc caagtccgt    660
caagatcttt atgcaatgtt acgtttctgg ttagataaag gcgtgtctgg tttacgtttt    720
gatacggtag cgacctactc aaaaattccg gatttcccaa atctcaccca acaacagctg    780
aagaattttg cagcggagta taccaagggc cctaatattc atcgttacgt caatgaaatg    840
aataaagagg tcttgtctca ttacgacatt gcgactgccg tgaaatcttt ggcgtaccc    900
ttggatcaat cgataaagtt cttcgatcgc cgccgtgatg agctgaacat tgcatttacc    960
tttgacttaa tcagactcga tcgatatcct gatcaaagat ggcgtcgaaa agattggaaa    1020
ttgtcgcaat tccggcagat catcgataac gttgaccgta ctgcaggaga atatggttgg    1080
aatgccttct tcttggataa ccacgacaat ccgcgcgctg tctcgcactt tggcgatgat    1140
cgcccacaat ggcgtgagcc atcggctaaa gcgcttgcaa ccttgacgct gactcaacga    1200
gcaacacctt ttatttatca aggttcagaa ttgggcatga ccaattaccc gtttaaagct    1260
attgatgaat tcgatgatat tgaggtgaaa ggttttttggc atgactacgt tgagacagga    1320
aaggtcaaag ccgacgagtt cttgcaaaat gtacgcctga cgagcaggga taacagccgg    1380
acgccgttcc aatgggatgg gagcaaaaat gcaggattca cgagcggaaa accttggttc    1440
```

```
                                            -continued
aaggtcaacc caaactacca ggaaatcaat gcagtaagtc aagtcacaca acccgactca    1500
gtatttaact attatcgtca gttgatcaag ataaggcatg acatcccggc actgacctat    1560
ggtacataca ccgatttgga tcctgcaaat gattcggtct acgcctatac acgcagcctt    1620
ggggcggaaa aatatcttgt tgttgttaac ttcaaggagc aaatgatgag atataaatta    1680
ccggataatt tatccattga gaaagtgatt atagacagca acagcaaaaa cgtggtgaaa    1740
aagaatgatt cattactcga gctaaaacca tggcagtcag gggtttataa actaaatcaa    1800
taa                                                                  1803
```

SUCROSE MUTASE WITH IMPROVED PRODUCT SPECIFICITY

CROSS REFERENCE TO RELATED APPLICATIONS

The present application is a U.S. National Phase of PCT/EP2010/007767, filed Dec. 18, 2010, which claims benefit of German Application Number 10 2009 060 935.0 filed Dec. 23, 2009, the contents of which is incorporated by reference herein in their entirety.

DESCRIPTION

Figure 1:
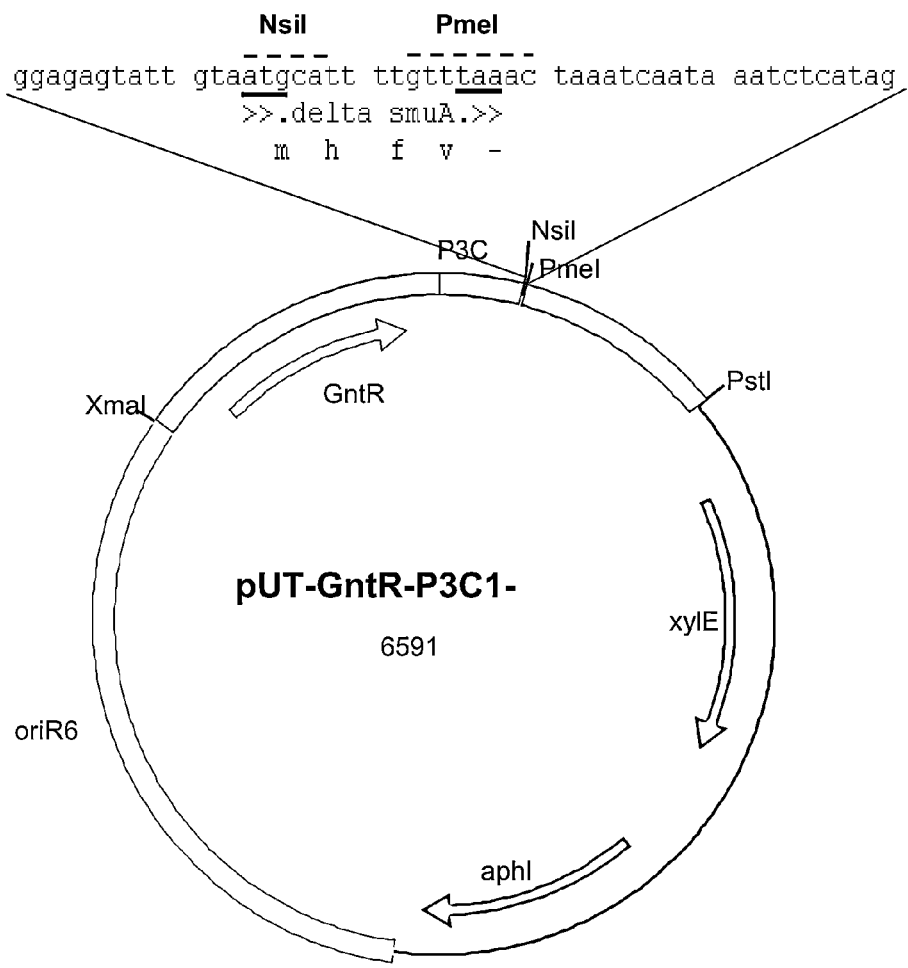
FIG. 1 shows as an example a vector map of the smuA-deletion plasmid pUT-GntR-P3C1-DSmuA, produced in relation to the invention, containing the substitution sequence of SEQ ID NO.: 1 (dark gray box). This area upstream from the smuA deletion area 1267 by exhibits homology to the *P. rubrum* chromosome. This area bears homologies to a GntR-type transcription regulator gene and the 3C1-promoter inserted without scar. 655 by homologous DNA sequence[s] are present downstream from the smuA deletion area. The actual deletion area of the smuA gene within the substitute sequence is enlarged and bolded as a nucleotide sequence. The native smuA start codon ATG and a TAA stop codon are underlined. Interface recognition sequences implemented for the restriction enzymes NsiI and PmeI are likewise marked by dotted lines. The pUT derivative is based on an R6K on ("origin of transfer") and for selection carries the kanamycin resistance gene aphII and the xylE gene, which codes for a catechol-2,3 dioxygenase.

The invention relates to the biotechnological production of isomaltulose and compositions containing isomaltulose from saccharose, and provides improved means for doing so, in particular a sucrose mutase with improved product specificity as well as microbial cells containing the improved sucrose mutase.

As is generally known, isomaltulose (palatinose) is producible from saccharose (cane sugar, beet sugar) in a biotechnological process by means of enzymatic isomerization. Isomaltulose is a physiologically valuable sugar that is gaining prominence as a saccharose substitute in foodstuffs and related products. Isomaltulose is not cariogenic and has a low glycemic index with basically the same energy content as saccharose. Isomaltulose has been approved for use in foodstuffs since 2005. Moreover, isomaltulose is a raw material used to produce the sugar alcohol isomalt, a racemic mixture of 1,6-GPS (6-O-α-D-glucopyranosyl-D-sorbite) and 1,1-GPM (1-O-α-D-glucopyranosyl-D-mannite) as well as modifications thereof, especially GPS- or GPM-enhanced mixtures.

The biotechnological production of isomaltulose from saccharose is done, as is known, using preferably immobilized bacteria cells or fragments of the same which exhibit the activity of the bacterial enzyme sucrose mutase, E.C. 5.4.99.11 (synonym: saccharose mutase, sucrose isomerase, saccharose isomerase, isomaltulose synthase). Microorganisms known to have sucrose mutase activity and that can be implemented in biotechnological processes are particularly *Protaminobacter rubrum*, *Erwinia rhapontici*, *Pseudomonas mesoacidophila*, *Pantoea dispersa* and *Serratia plymuthica*. Their endogenic sucrose mutase(s) are known by the abbreviations SmuA, Pal I, SmtA, MutB, SIM and others. Sucrose mutases are encoded by a chromosomal gene.

In the well-established biotechnological systems, saccharose is not fully enzymatically isomerized into isomaltulose. Rather, other isomerization products and secondary products are produced. Another important isomerization product is trehalulose. A sucrose mutase SmuA is present in the microorganism *Protaminobacter rubrum*, whose product specificity is designed such that saccharose is isomerized into isomaltulose only up to about 85% even under optimized cultivation conditions. The product specificity of sucrose mutase SmuA is in need of improvement. But the technical production of isomaltulose with biotechnological means is based on the sucrose mutase SmuA from *P. rubrum*.

The present invention has therefore set itself the task of providing an improved SmuA-based sucrose mutase as well as a microorganism containing such improved sucrose mutase that features improved product specificity and selectivity for isomaltulose, through which the amount of isomaltulose in the isomerization product is increased, making it possible to carry out the transformation of saccharose into isomaltulose more efficiently in otherwise well-established biotechnological processes as well. In this regard, the invention has set itself the particular task of providing an improved SmuA-based sucrose mutase that can be used in basically unchanged, already established industrial biotechnological processes, without costly modifications of reaction conditions and procedures having to be made in the established processes. The use of sucrose mutases from other organisms and switching to new biotechnological processes should be avoided.

The technical problem on which the invention is based is fully solved by providing a novel polyamino acid molecule that features improved sucrose mutase activity with respect to the transformation of saccharose into isomaltulose, i.e., a higher product specificity for isomaltulose. According to the invention the improved sucrose mutase exhibits an amino acid sequence that is preferably directly derived from the wild-type sequence of the sucrose mutase SmuA from *Protaminobacter rubrum*, whereby in at least one of the amino acid positions mentioned below, relative to the position number of a wild-type sequence that is shown in SEQ ID No. 1, [sic] features one or more of the amino acid substitutes listed below: 5303P, D302Y, K180P, M199I, Q276A, A198D, Y219F, V324T, T369L and A346Q as well as combinations of two, three, four, five, six, seven, eight, nine or all ten. When doing so, according to the invention the position is determined based on the location of the active center.

Accordingly, the invention provides as a solution: An improved novel sucrose mutase enzyme, characterized in that it features, exclusively features or contains a modified amino acid sequence selected from the group of amino acid sequences that for the sequence shown in SEQ ID NO: 1 feature one or more of the following amino acid substitutions: 5303P, D302Y, K180P, M199I, Q276A, A198D, Y219F, V324T, T369L and A346Q.

The invention also relates to a functional modification thereof, i.e., a polyamino acid molecule that features, exclusively features or contains segments of such amino acid sequence modified according to the invention, of the sequence shown in SEQ ID NO: 1, to the extent such polyamino acid molecule exhibits the function of the improved novel sucrose mutase enzyme according to the invention. The expert can easily produce equivalent functional modifications from the sequence data stated herein, and test for their function as a sucrose mutase enzyme in a well-established manner.

In a first embodiment of the invention the amino acid substitution is at position S303; amino acid P is preferably substituted.

In an alternative or additional embodiment of the invention the amino acid substitution is at position D302; amino acid Y is preferably substituted. A combination of the substitutions 5303P and D302Y is especially preferred.

In an alternative or additional embodiment of the invention the amino acid substitution is at position K180; amino acid P is preferably substituted.

In an alternative or additional embodiment of the invention the amino acid substitution is at position M199: amino acid I is preferably substituted (M199I).

In an alternative or additional embodiment of the invention the amino acid substitution is at position Q276; amino acid A is preferably substituted.

In an alternative or additional embodiment of the invention the amino acid substitution is at position A198; amino acid D is preferably substituted.

In an alternative or additional embodiment of the invention the amino acid substitution is at position Y219; amino acid F is preferably substituted.

In an alternative or additional embodiment of the invention the amino acid substitution is at position V324; amino acid T is preferably substituted.

In an alternative or additional embodiment of the invention the amino acid substitution is at position T369; amino acid L is preferably substituted.

In an alternative or additional embodiment of the invention the amino acid substitution is at position A346; amino acid Q is preferably substituted.

Besides the preferred combinations of multiple amino acid substitutions described in detail below, the following additional amino acids are possible individually or in combination: M199I in combination with V114I, Q122R, Q276A, N423E, L426I, L426F.

Also preferred is a combination of S303P with at least one other or exactly one other selected from the group comprising: D302Y, K180P, M199I, Q276A, A198D, Y219F, V324T, T369L and A346Q. One preferred combination is S303P+D302Y. Another preferred combination is S303P+M199I. Another preferred combination is S303P+Q276A. Another preferred combination is S303P+A198D. Another preferred combination is S303P+Y219F. Another preferred combination is S303P+V324T. Another preferred combination is S303P+T369L. Another preferred combination is S303P+A346Q.

A combination of S303P and D302Y with at least one other or exactly one other selected from the group comprising: K180P, M199I, Q276A, A198D, Y219F, V324T, T369L and A346Q is also preferred.

A combination of S303P and K180P with at least one other or exactly one other selected from the group comprising: D302Y, M199I, Q276A, A198D, Y219F, V324T, T369L and A346Q is also preferred.

A combination of S303P and M199I with at least one other or exactly one other selected from the group comprising: D302Y, K180P, Q276A, A198D, Y219F, V324T, T369L and A346Q is also preferred.

A combination of S303P and Q276A with at least one other or exactly one other selected from the group comprising: D302Y, K180P, M199I, A198D, Y219F, V324T, T369L and A346Q is also preferred.

A combination of S303P and A198D with at least one other or exactly one other selected from the group comprising: D302Y, K180P, M199I, Q276A, Y219F, V324T, T369L and A346Q is also preferred.

A combination of S303P and Y219F with at least one other or exactly one other selected from the group comprising: D302Y, K180P, M199I, Q276A, A198D, V324T, T369L and A346Q is also preferred.

A combination of S303P and V324T with at least one other or exactly one other selected from the group comprising: D302Y, K180P, M199I, Q276A, A198D, Y219F, T369L and A346Q is also preferred.

A combination of S303P and T369L with at least one other or exactly one other selected from the group comprising: D302Y, K180P, M199I, Q276A, A198D, Y219F, V324T and A346Q is also preferred.

A combination of S303P and A346Q with at least one other or exactly one other selected from the group comprising: D302Y, K180P, M199I, Q276A, A198D, Y219F, V324T and T369L is also preferred.

A preferred combination thereof is S303P+D302Y+ K180P. In other variants this combination is additionally combined with one or several of the following: M199I, Q276A, A198D, Y219F, V324T, T369L and A346Q. S303P+ D302Y+K180P+S303P+D302Y+K180P+M199I, S303P+ D302Y+K180P+S303P+D302Y+K180P+Q276A, S303P+ D302Y+K180P+A198D, S303P+D302Y+K180P+Y219F, S303P+D302Y+K180P+V324T, S303P+D302Y+K180P+ T369L and/or S303P+D302Y+K180P+A346Q is preferred.

Another preferred combination is S303P+D302Y+M199I. In other variants this combination is additionally combined with one or several of the following: K180P, Q276A, A198D, Y219F, V324T, T369L and A346Q. S303P+D302Y+M199I+ S303P+D302Y+M199I+Q276A, S303P+D302Y+M199I+ A198D, S303P+D302Y+M199I+Y219F, S303P+D302Y+ M199I+V324T, S303P+D302Y+M199I+T369L and/or S303P+D302Y+M199I+A346Q is preferred. Other preferred embodiments thereof are mentioned above.

Another preferred combination is S303P+D302Y+ Q276A. In other variants this combination is additionally combined with one or several of the following: K180P, M199I, A198D, Y219F, V324T, T369L and A346Q. S303P+ D302Y+Q276A+A198D, S303P+D302Y+Q276A+Y219F, S303P+D302Y+Q276A+V324T, S303P+D302Y+Q276A+ T369L, S303P+D302Y+Q276A+A346Q is preferred. Other preferred embodiments thereof are mentioned above.

Another preferred combination is S303P+D302Y+ A198D. In other variants this combination is additionally combined with one or several of the following: K180P, M199I, Q276A, Y219F, V324T, T369L and A346Q. S303P+ D302Y+A198D+Y219F, S303P+D302Y+A198D+V324T, S303P+D302Y+A198D+T369L and/or S303P+D302Y+ A198D+A346Q is preferred. Other preferred embodiments thereof are mentioned above.

Another preferred combination is S303P+D302Y+Y219F. In other variants this combination is additionally combined with one or several of the following: K180P, M199I, Q276A, A198D, V324T, T369L and A346Q. S303P+D302Y+ Y219F+V324T, S303P+D302Y+Y219F+T369L and/or S303P+D302Y+Y219F+A346Q is preferred. Other preferred embodiments thereof are mentioned above.

Another preferred combination is S303P+D302Y+V324T. In other variants this combination is additionally combined with one or several of the following: K180P, M199I, Q276A, A198D, Y219F, T369L and A346Q. S303P+D302Y+ V324T+T369L and/or S303P+D302Y+V324T+A346Q is preferred. Other preferred embodiments thereof are mentioned above.

Another preferred combination is S303P+D302Y+T369L. In other variants this combination is additionally combined with one or several of the following: K180P, M199I, Q276A, A198D, Y219F, V324T and A346Q. S303P+D302Y+ T369L+A346Q is preferred. Other preferred embodiments thereof are mentioned above.

Another preferred combination is S303P+D302Y+ A346Q. In other variants this combination is additionally combined with one or several of the following: K180P, M199I, Q276A, A198D, Y219F, V324T and T369L. Other preferred embodiments thereof are mentioned above.

Another preferred combination is S303P+K180P+M199I. In other variants this combination is additionally combined with one or several of the following: D302Y, Q276A, A198D, Y219F, V324T, T369L and A346Q. S303P+K180P+M199I+ S303P+K180P+M199I+Q276A, S303P+K180P+M199I+ A198D, S303P+K180P+M199I+Y219F, S303P+K180P+ M199I+V324T, S303P+K180P+M199I+T369L and/or S303P+K180P+M199I+A346Q is preferred. Other preferred embodiments thereof are mentioned above.

Another preferred combination is S303P+K180P+Q276A. In other variants this combination is additionally combined with one or several of the following: D302Y, M199I, A198D, Y219F, V324T, T369L and A346Q. S303P+K180P+Q276A+ A198D, S303P+K180P+Q276A+Y219F, S303P+K180P+ Q276A+V324T, S303P+K180P+Q276A+T369L and/or S303P+K180P+Q276A+A346Q is preferred. Other preferred embodiments thereof are mentioned above.

Another preferred combination is S303P+K180P+A198D. In other variants this combination is additionally combined with one or several of the following: D302Y, M199I, Q276A, Y219F, V324T, T369L and A346Q. S303P+K180P+A198D+ Y219F, S303P+K180P+A198D+V324T, S303P+K180P+ A198D+T369L and/or S303P+K180P+A198D+A346Q is preferred. Other preferred embodiments thereof are mentioned above.

Another preferred combination is S303P+K180P+Y219F. In other variants this combination is additionally combined with one or several of the following: D302Y, M199I, Q276A, A198D, V324T, T369L and A346Q. S303P+K180P+ Y219F+V324T, S303P+K180P+Y219F+T369L and/or S303P+K180P+Y219F+A346Q is preferred. Other preferred embodiments thereof are mentioned above.

Another preferred combination is S303P+K180P+V324T. In other variants this combination is additionally combined with one or several of the following: D302Y, M199I, Q276A, A198D, Y219F, T369L and A346Q. S303P+K180P+V324T+ T369L and/or S303P+K180P+V324T+A346Q is preferred. Other preferred embodiments thereof are mentioned above.

Another preferred combination is S303P+K180P+T369L. In other variants this combination is additionally combined with one or several of the following: D302Y, M199I, Q276A, A198D, Y219F, V324T and A346Q. S303P+K180P+T369L+ A346Q is preferred. Other preferred embodiments thereof are mentioned above.

Another preferred combination is S303P+K180P+A346Q. In other variants this combination is additionally combined with one or several of the following: D302Y, M199I, Q276A, A198D, Y219F, V324T and T369L. Other preferred embodiments thereof are mentioned above.

Another preferred combination is S303P+M199I+Q276A. In other variants this combination is additionally combined with one or several of the following: D302Y, K180P, A198D, Y219F, V324T, T369L and A346Q. S303P+M199I+Q276A+ S303P+M199I+Q276A+A198D, S303P+M199I+Q276A+ Y219F, S303P+M199I+Q276A+V324T, and/or S303P+ M199I+Q276A+T369L, S303P+M199I+Q276A+A346Q is preferred. Other preferred embodiments thereof are mentioned above.

Another preferred combination is S303P+M199I+A198D. In other variants this combination is additionally combined with one or several of the following: D302Y, K180P, Q276A, Y219F, V324T, T369L and A346Q. S303P+M199I+A198D+ Y219F, S303P+M199I+A198D+V324T, S303P+M199I+ A198D+T369L and/or S303P+M199I+A198D+A346Q is preferred. Other preferred embodiments thereof are mentioned above.

Another preferred combination is S303P+M199I+Y219F. In other variants this combination is additionally combined with one or several of the following: D302Y, K180P, Q276A, A198D, V324T, T369L and A346Q. S303P+M199I+Y219F+ V324T and/or S303P+M199I+Y219F+T369L, S303P+ M199I+Y219F+A346Q is preferred. Other preferred embodiments thereof are mentioned above.

Another preferred combination is S303P+M199I+V324T. In other variants this combination is additionally combined with one or several of the following: D302Y, K180P, Q276A, A198D, Y219F, T369L and A346Q. S303P+M199I+V324T+ T369L and/or S303P+M199I+V324T+A346Q is preferred. Other preferred embodiments thereof are mentioned above.

Another preferred combination is S303P+M199I+T369L. In other variants this combination is additionally combined with one or several of the following: D302Y, K180P, Q276A, A198D, Y219F, V324T and A346Q. S303P+M199I+T369L+ A346Q is preferred. Other preferred embodiments thereof are mentioned above.

Another preferred combination is S303P+M199I+A346Q. In other variants this combination is additionally combined with one or several of the following: D302Y, K180P, Q276A, A198D, Y219F, V324T and T369L. Other preferred embodiments thereof are mentioned above.

Another preferred combination is S303P+Q276A+ A198D. In other variants this combination is additionally combined with one or several of the following: D302Y, K180P, M199I, Y219F, V324T, T369L and A346Q. S303P+ Q276A+A198D+Y219F, S303P+Q276A+A198D+V324T, S303P+Q276A+A198D+T369L and/or S303P+Q276A+ A198D+A346Q is preferred. Other preferred embodiments thereof are mentioned above.

Another preferred combination is S303P+Q276A+Y219F. In other variants this combination is additionally combined with one or several of the following: D302Y, K180P, M199I, A198D, V324T, T369L and, A346Q. S303P+Q276A+ Y219F+V324T, S303P+Q276A+Y219F+T369L and/or S303P+Q276A+Y219F+A346Q is preferred. Other preferred embodiments thereof are mentioned above.

Another preferred combination is S303P+Q276A+V324T. In other variants this combination is additionally combined with one or several of the following: D302Y, K180P, M199I, A198D, Y219F, T369L and A346Q. S303P+Q276A+ V324T+T369L, and/or S303P+Q276A+V324T+A346Q is preferred. Other preferred embodiments thereof are mentioned above.

Another preferred combination is S303P+Q276A+T369L. In other variants this combination is additionally combined with one or several of the following: D302Y, K180P, M199I, A198D, Y219F, V324T and A346Q. S303P+Q276A+ T369L+A346Q is preferred. Other preferred embodiments thereof are mentioned above.

Another preferred combination is S303P+Q276A+ A346Q. In other variants this combination is additionally combined with one or several of the following: D302Y, K180P, M199I, A198D, Y219F, V324T and T369L. Other preferred embodiments thereof are mentioned above.

Another preferred combination is S303P+A198D+Y219F. In other variants this combination is additionally combined with one or several of the following: D302Y, K180P, M199I, Q276A, V324T, T369L and A346Q. S303P+A198D+ Y219F+V324T, S303P+A198D+Y219F+T369L and/or S303P+A198D+Y219F+A346Q is preferred. Other preferred embodiments thereof are mentioned above.

Another preferred combination is S303P+A198D+V324T. In other variants this combination is additionally combined with one or several of the following: D302Y, K180P, M199I, Q276A, Y219F, T369L and A346Q. S303P+A198D+ V324T+T369L, S303P+A198D+V324T+A346Q is preferred. Other preferred embodiments thereof are mentioned above.

Another preferred combination is S303P+A198D+T369L. In other variants this combination is additionally combined with one or several of the following: D302Y, K180P, M199I, Q276A, Y219F, V324T and A346Q. S303P+A198D+ T369L+A346Q is preferred. Other preferred embodiments thereof are mentioned above.

Another preferred combination is S303P+A198D+ A346Q. In other variants this combination is additionally combined with one or several of the following: D302Y, K180P, M199I, Q276A, Y219F, V324T and T369L. Other preferred embodiments thereof are mentioned above.

Another preferred combination is S303P+Y219F+V324T. In other variants this combination is additionally combined with one or several of the following: D302Y, K180P, M199I, Q276A, A198D, T369L and A346Q. S303P+Y219F+ V324T+T369L and/or S303P+Y219F+V324T+A346Q is preferred. Other preferred embodiments thereof are mentioned above.

Another preferred combination is S303P+Y219F+T369L. In other variants this combination is additionally combined with one or several of the following: D302Y, K180P, M199I, Q276A, A198D, V324T and A346Q. S303P+Y219F+ T369L+A346Q is preferred. Other preferred embodiments thereof are mentioned above.

Another preferred combination is S303P+Y219F+A346Q. In other variants this combination is additionally combined with one or several of the following: D302Y, K180P, M199I, Q276A, A198D, V324T and T369L. Other preferred embodiments thereof are mentioned above.

Another preferred combination is S303P+V324T+T369L. In other variants this combination is additionally combined with one or several of the following: D302Y, K180P, M199I, Q276A, A198D, Y219F and A346Q. S303P+V324T+ T369L+A346Q is preferred. Other preferred embodiments thereof are mentioned above.

Another preferred combination is S303P+V324T+A346Q. In other variants this combination is additionally combined with one or several of the following: D302Y, K180P, M199I, Q276A, A198D, Y219F and T369L. Other preferred embodiments thereof are mentioned above.

Another preferred combination is S303P+T369L+A346Q. In other variants this combination is additionally combined with one or several of the following: D302Y, K180P, M199I, Q276A, A198D, Y219F and V324T. Other preferred embodiments thereof are mentioned above.

A combination of D302Y with at least one other or exactly one other selected from the group comprising: S303P, K180P, M199I, Q276A, A198D, Y219F, V324T, T369L and A346Q is preferred. One preferred combination is D302Y+K180P. Another preferred combination is D302Y+M199I. Another preferred combination is D302Y+Q276A. Another preferred combination is D302Y+A198D. Another preferred combination is D302Y+Y219F. Another preferred combination is D302Y+V324T. Another preferred combination is D302Y+ T369L. Another preferred combination is D302Y+A346Q.

A combination of D302Y and K180P with at least one other or exactly one other selected from the group comprising: S303P, M199I, Q276A, A198D, Y219F, V324T, T369L and A346Q is also preferred.

A combination of D302Y and M199I with at least one other or exactly one other selected from the group comprising: S303P, K180P, Q276A, A198D, Y219F, V324T, T369L and A346Q is also preferred.

A combination of D302Y and Q276A with at least one other or exactly one other selected from the group comprising: S303P, K180P, A198D, Y219F, V324T, T369L and A346Q is also preferred.

A combination of D302Y and A198D with at least one other or exactly one other selected from the group comprising: S303P, K180P, M199I, Q276A, Y219F, V324T, T369L and A346Q is also preferred.

A combination of D302Y and Y219F with at least one other or exactly one other selected from the group comprising: S303P, K180P, M199I, Q276A, A198D, V324T, T369L and A346Q is also preferred.

A combination of D302Y and V324T with at least one other or exactly one other selected from the group comprising: S303P, K180P, M199I, Q276A, A198D, Y219F, T369L and A346Q is also preferred.

A combination of D302Y and T369L with at least one other or exactly one other selected from the group comprising: S303P, K180P, M199I, Q276A, A198D, Y219F, V324T and A346Q is also preferred.

A combination of D302Y and A346Q with at least one other or exactly one other selected from the group comprising: S303P, K180P, M199I, Q276A, A198D, Y219F, V324T and T369L is also preferred.

A combination of D302Y and at least one other or exactly one other selected from the group comprising: S303P, K180P, M199I, Q276A, A198D, Y219F, V324T, T369L and A346Q is also preferred.

Another preferred combination is D302Y+K180P+M199I. In other variants this combination is additionally combined with one or several of the following: S303P, Q276A, A198D, Y219F, V324T, T369L and A346Q. D302Y+K180P+M199I+D302Y+K180P+M199I+Q276A, D302Y+K180P+M199I+A198D, D302Y+K180P+M199I+Y219F, D302Y+K180P+M199I+V324T, D302Y+K180P+M199I+T369L and/or D302Y+K180P+M199I+A346Q is preferred. Other preferred embodiments thereof are mentioned above.

Another preferred combination is D302Y+K180P+Q276A. In other variants this combination is additionally combined with one or several of the following: S303P, M199I, A198D, Y219F, V324T, T369L and A346Q. D302Y+K180P+Q276A+A198D, D302Y+K180P+Q276A+Y219F, D302Y+K180P+Q276A+V324T, D302Y+K180P+Q276A+T369L and/or D302Y+K180P+Q276A+A346Q [sic: is preferred]. Other preferred embodiments thereof are mentioned above.

Another preferred combination is D302Y+K180P+A198D. In other variants this combination is additionally combined with one or several of the following: S303P, M199I, Q276A, Y219F, V324T, T369L and A346Q. D302Y+K180P+A198D+Y219F, D302Y+K180P+A198D+V324T, D302Y+K180P+A198D+T369L and/or D302Y+K180P+A198D+A346Q is preferred. Other preferred embodiments thereof are mentioned above.

Another preferred combination is D302Y+K180P+Y219F. In other variants this combination is additionally combined with one or several of the following: S303P, M199I, Q276A, A198D, V324T, T369L and A346Q. D302Y+K180P+Y219F+V324T, D302Y+K180P+Y219F+T369L and/or D302Y+K180P+Y219F+A346Q is preferred. Other preferred embodiments thereof are mentioned above.

Another preferred combination is D302Y+K180P+V324T. In other variants this combination is additionally combined with one or several of the following: S303P, M199I, Q276A, A198D, Y219F, T369L and A346Q. D302Y+K180P+V324T+T369L and/or D302Y+K180P+V324T+A346Q is preferred. Other preferred embodiments thereof are mentioned above.

Another preferred combination is D302Y+K180P+T369L. In other variants this combination is additionally combined with one or several of the following: S303P, M199I, Q276A, A198D, Y219F, V324T and A346Q. D302Y+K180P+T369L+A346Q is preferred. Other preferred embodiments thereof are mentioned above.

Another preferred combination is D302Y+K180P+A346Q. In other variants this combination is additionally combined with one or several of the following: S303P, M199I, Q276A, A198D, Y219F, V324T and T369L. Other preferred embodiments thereof are mentioned above.

Another preferred combination is D302Y+M199I+Q276A. In other variants this combination is additionally combined with one or several of the following: S303P, K180P, A198D, Y219F, V324T, T369L and A346Q. D302Y+M199I+Q276A+A198D, D302Y+M199I+Q276A+Y219F, D302Y+M199I+Q276A+V324T, and/or D302Y+M199I+Q276A+T369L, D302Y+M199I+Q276A+A346Q is preferred. Other preferred embodiments thereof are mentioned above.

Another preferred combination is D302Y+M199I+A198D. In other variants this combination is additionally combined with one or several of the following: S303P, K180P, Q276A, Y219F, V324T, T369L and A346Q. D302Y+M199I+A198D+Y219F, D302Y+M199I+A198D+V324T, D302Y+M199I+A198D+T369L and/or D302Y+M199I+A198D+A346Q is preferred. Other preferred embodiments thereof are mentioned above.

Another preferred combination is D302Y+M199I+Y219F. In other variants this combination is additionally combined with one or several of the following: S303P, K180P, Q276A, A198D, V324T, T369L and A346Q. D302Y+M199I+Y219F+V324T, D302Y+M199I+Y219F+T369L and/or D302Y+M199I+Y219F+A346Q is preferred. Other preferred embodiments thereof are mentioned above.

Another preferred combination is D302Y+M199I+V324T. In other variants this combination is additionally combined with one or several of the following: S303P, K180P, Q276A, A198D, Y219F, T369L and A346Q. D302Y+M199I+V324T+T369L, D302Y+M199I+V324T+A346Q is preferred. Other preferred embodiments thereof are mentioned above.

Another preferred combination is D302Y+M199I+T369L. In other variants this combination is additionally combined with one or several of the following: S303P, K180P, Q276A, A198D, Y219F, V324T and A346Q. D302Y+M199I+T369L+A346Q is preferred. Other preferred embodiments thereof are mentioned above.

Another preferred combination is D302Y+M199I+A346Q. In other variants this combination is additionally combined with one or several of the following: S303P, K180P, Q276A, A198D, Y219F, V324T and T369L is preferred. Other preferred embodiments thereof are mentioned above.

Another preferred combination is D302Y+Q276A+A198D. In other variants this combination is additionally combined with one or several of the following: S303P, K180P, M199I, Y219F, V324T, T369L and A346Q. D302Y+Q276A+A198D+Y219F, D302Y+Q276A+A198D+V324T, D302Y+Q276A+A198D+T369L, and/or D302Y+Q276A+A198D+A346Q is preferred. Other preferred embodiments thereof are mentioned above.

Another preferred combination is D302Y+Q276A+Y219F. In other variants this combination is additionally combined with one or several of the following: S303P, K180P, M199I, A198D, V324T, T369L and A346Q. D302Y+Q276A+Y219F+V324T and/or D302Y+Q276A+Y219F+T369L, D302Y+Q276A+Y219F+A346Q is preferred. Other preferred embodiments thereof are mentioned above.

Another preferred combination is D302Y+Q276A+V324T. In other variants this combination is additionally combined with one or several of the following: S303P, K180P, M199I, A198D, Y219F, T369L and A346Q. D302Y+Q276A+V324T+T369L, D302Y+Q276A+V324T+A346Q is preferred. Other preferred embodiments thereof are mentioned above.

Another preferred combination is D302Y+Q276A+T369L. In other variants this combination is additionally combined with one or several of the following: S303P, K180P, M199I, A198D, Y219F, V324T and A346Q. D302Y+Q276A+T369L+A346Q is preferred. Other preferred embodiments thereof are mentioned above.

Another preferred combination is D302Y+Q276A+A346Q. In other variants this combination is additionally combined with one or several of the following: S303P, K180P, M199I, A198D, Y219F, V324T and T369L. Other preferred embodiments thereof are mentioned above.

Another preferred combination is D302Y+A198D+V324T. In other variants this combination is additionally combined with one or several of the following: S303P, K180P, M199I, Q276A, Y219F, T369L and A346Q. D302Y+A198D+V324T+T369L and/or D302Y+A198D+V324T+A346Q is preferred. Other preferred embodiments thereof are mentioned above.

Another preferred combination is D302Y+A198D+T369L. In other variants this combination is additionally combined with one or several of the following: S303P, K180P, M199I, Q276A, Y219F, V324T and A346Q. D302Y+A198D+T369L+A346Q is preferred. Other preferred embodiments thereof are mentioned above.

Another preferred combination is D302Y+A198D+A346Q. In other variants this combination is additionally combined with one or several of the following: S303P, K180P, M199I, Q276A, Y219F, V324T and T369L. Other preferred embodiments thereof are mentioned above.

Another preferred combination is D302Y+Y219F+V324T. In other variants this combination is additionally combined with one or several of the following: S303P, K180P, M199I, Q276A, A198D, T369L and A346Q. D302Y+Y219F+V324T+T369L, D302Y+Y219F+V324T+A346Q is preferred. Other preferred embodiments thereof are mentioned above.

Another preferred combination is D302Y+Y219F+T369L. In other variants this combination is additionally combined with one or several of the following: S303P, K180P, M199I, Q276A, A198D, V324T and A346Q. D302Y+Y219F+T369L+A346Q is preferred. Other preferred embodiments thereof are mentioned above.

Another preferred combination is D302Y+Y219F+A346Q. In other variants this combination is additionally combined with one or several of the following: S303P, K180P, M199I, Q276A, A198D, V324T and T369L. Other preferred embodiments thereof are mentioned above.

Another preferred combination is D302Y+V324T+T369L. In other variants this combination is additionally combined with one or several of the following: S303P, K180P, M199I, Q276A, A198D, Y219F and A346Q. D302Y+V324T+T369L+A346Q is preferred. Other preferred embodiments thereof are mentioned above.

Another preferred combination is D302Y+V324T+A346Q. In other variants this combination is additionally combined with one or several of the following: S303P, K180P, M199I, Q276A, A198D, Y219F and T369L. Other preferred embodiments thereof are mentioned above.

Another preferred combination is D302Y+T369L+A346Q. In other variants this combination is additionally combined with one or several of the following: S303P, K180P, M199I, Q276A, A198D, Y219F and V324T. Other preferred embodiments thereof are mentioned above.

A combination of K180P with at least one other or exactly one other selected from the group comprising: S303P, D302Y, M199I, Q276A, A198D, Y219F, V324T, T369L and A346Q is preferred. Another preferred combination is K180P+Q276A. Another preferred combination is K180P+A198D. Another preferred combination is K180P+Y219F. Another preferred combination is K180P+V324T. Another preferred combination is K180P+T369L. Another preferred combination is K180P+A346Q.

A combination of K180P and M199I with at least one other or exactly one other selected from the group comprising: S303P, D302Y, Q276A, A198D, Y219F, V324T, T369L and A346Q is also preferred.

A combination of K180P and Q276A with at least one other or exactly one other selected from the group comprising: S303P, D302Y, M199I, A198D, Y219F, V324T, T369L and A346Q is also preferred.

A combination of K180P and A198D with at least one other or exactly one other selected from the group comprising: S303P, D302Y, M199I, Q276A, Y219F, V324T, T369L and A346Q is also preferred.

A combination of K180P and Y219F with at least one other or exactly one other selected from the group comprising: S303P, D302Y, M199I, Q276A, A198D, V324T, T369L and A346Q is also preferred.

A combination of K180P and V324T with at least one other or exactly one other selected from the group comprising: S303P, D302Y, M199I, Q276A, A198D, Y219F, T369L and A346Q is also preferred.

A combination of K180P and T369L with at least one other or exactly one other selected from the group comprising: S303P, D302Y, M199I, Q276A, A198D, Y219F, V324T and A346Q is also preferred.

A combination of K180P and A346Q with at least one other or exactly one other selected from the group comprising: S303P, D302Y, M199I, Q276A, A198D, Y219F, V324T and T369L is also preferred.

Another preferred combination is K180P+M199I+Q276A. In other variants this combination is additionally combined with one or several of the following: S303P, D302Y, A198D, Y219F, V324T, T369L and A346Q. K180P+M199I+Q276A+A198D, K180P+M199I+Q276A+Y219F, K180P+M199I+Q276A+V324T, K180P+M199I+Q276A+T369L and/or K180P+M199I+Q276A+A346Q [sic: is preferred]. Other preferred embodiments thereof are mentioned above.

Another preferred combination is K180P+M199I+A198D. In other variants this combination is additionally combined with one or several of the following: S303P, D302Y, Q276A, Y219F, V324T, T369L and A346Q. K180P+M199I+A198D+Y219F, K180P+M199I+A198D+V324T, K180P+M199I+A198D+T369L and/or K180P+M199I+A198D+A346Q is preferred. Other preferred embodiments thereof are mentioned above.

Another preferred combination is K180P+M199I+Y219F. In other variants this combination is additionally combined with one or several of the following: S303P, D302Y, Q276A, A198D, V324T, T369L and A346Q. K180P+M199I+Y219F+V324T, K180P+M199I+Y219F+T369L and/or K180P+M199I+Y219F+A346Q is preferred. Other preferred embodiments thereof are mentioned above.

Another preferred combination is K180P+M199I+V324T. In other variants this combination is additionally combined with one or several of the following: S303P, D302Y, Q276A, A198D, Y219F, T369L and A346Q. K180P+M199I+

V324T+T369L, K180P+M199I+V324T+A346Q is preferred. Other preferred embodiments thereof are mentioned above.

Another preferred combination is K180P+M199I+T369L. In other variants this combination is additionally combined with one or several of the following: S303P, D302Y, Q276A, A198D, Y219F, V324T and A346Q. K180P+M199I+T369L+A346Q is preferred. Other preferred embodiments thereof are mentioned above.

Another preferred combination is K180P+M199I+A346Q. In other variants this combination is additionally combined with one or several of the following: S303P, D302Y, Q276A, A198D, Y219F, V324T and T369L. Other preferred embodiments thereof are mentioned above.

Another preferred combination is K180P+Q276A+A198D. In other variants this combination is additionally combined with one or several of the following: S303P, D302Y, M199I, Y219F, V324T, T369L and A346Q. K180P+Q276A+A198D+Y219F, K180P+Q276A+A198D+V324T, K180P+Q276A+A198D+T369L and/or K180P+Q276A+A198D+A346Q is preferred. Other preferred embodiments thereof are mentioned above.

Another preferred combination is K180P+Q276A+Y219F. In other variants this combination is additionally combined with one or several of the following: S303P, D302Y, M199I, A198D, V324T, T369L and A346Q. K180P+Q276A+Y219F+V324T, K180P+Q276A+Y219F+T369L, and/or K180P+Q276A+Y219F+A346Q is preferred. Other preferred embodiments thereof are mentioned above.

Another preferred combination is K180P+Q276A+V324T. In other variants this combination is additionally combined with one or several of the following: S303P, D302Y, M199I, A198D, Y219F, T369L and A346Q. K180P+Q276A+V324T+T369L and/or K180P+Q276A+V324T+A346Q is preferred. Other preferred embodiments thereof are mentioned above.

Another preferred combination is K180P+Q276A+T369L. In other variants this combination is additionally combined with one or several of the following: S303P, D302Y, M199I, A198D, Y219F, V324T and A346Q. K180P+Q276A+T369L+A346Q is preferred. Other preferred embodiments thereof are mentioned above.

Another preferred combination is K180P+Q276A+A346Q. In other variants this combination is additionally combined with one or several of the following: S303P, D302Y, M199I, A198D, Y219F, V324T and T369L. Other preferred embodiments thereof are mentioned above.

Another preferred combination is K180P+A198D+Y219F. In other variants this combination is additionally combined with one or several of the following: S303P, D302Y, M199I, Q276A, V324T, T369L and A346Q. K180P+A198D+Y219F+V324T, K180P+A198D+Y219F+T369L and/or K180P+A198D+Y219F+A346Q is preferred. Other preferred embodiments thereof are mentioned above.

Another preferred combination is K180P+A198D+V324T. In other variants this combination is additionally combined with one or several of the following: S303P, D302Y, M199I, Q276A, Y219F, T369L and A346Q. K180P+A198D+V324T+T369L and/or K180P+A198D+V324T+A346Q is preferred. Other preferred embodiments thereof are mentioned above.

Another preferred combination is K180P+A198D+T369L. In other variants this combination is additionally combined with one or several of the following: S303P, D302Y, M199I, Q276A, Y219F, V324T and A346Q. K180P+A198D+T369L+A346Q. Other preferred embodiments thereof are mentioned above.

Another preferred combination is K180P+A198D+A346Q. In other variants this combination is additionally combined with one or several of the following: S303P, D302Y, M199I, Q276A, Y219F, V324T and T369L is preferred. Other preferred embodiments thereof are mentioned above.

Another preferred combination is K180P+Y219F+V324T. In other variants this combination is additionally combined with one or several of the following: S303P, D302Y, M199I, Q276A, A198D, T369L and A346Q. K180P+Y219F+V324T+T369L, K180P+Y219F+V324T+A346Q is preferred. Other preferred embodiments thereof are mentioned above.

Another preferred combination is K180P+Y219F+T369L. In other variants this combination is additionally combined with one or several of the following: S303P, D302Y, M199I, Q276A, A198D, V324T and A346Q. K180P+Y219F+T369L+A346Q is preferred. Other preferred embodiments thereof are mentioned above.

Another preferred combination is K180P+Y219F+A346Q. In other variants this combination is additionally combined with one or several of the following: S303P, D302Y, M199I, Q276A, A198D, V324T and T369L. Other preferred embodiments thereof are mentioned above.

Another preferred combination is K180P+V324T+T369L. In other variants this combination is additionally combined with one or several of the following: S303P, D302Y, M199I, Q276A, A198D, Y219F and A346Q. K180P+V324T+T369L+A346Q is preferred. Other preferred embodiments thereof are mentioned above.

Another preferred combination is K180P+V324T+A346Q. In other variants this combination is additionally combined with one or several of the following: S303P, D302Y, M199I, Q276A, A198D, Y219F and T369L. Other preferred embodiments thereof are mentioned above.

Another preferred combination is K180P+T369L+A346Q. In other variants this combination is additionally combined with one or several of the following: S303P, D302Y, M199I, Q276A, A198D, Y219F and V324T. Other preferred embodiments thereof are mentioned above.

A combination of M199I with at least one other or exactly one other selected from the group comprising: S303P, D302Y, K180P, Q276A, A198D, Y219F, V324T, T369L and A346Q is preferred. Another preferred combination is M199I+Q276A. Another preferred combination is M199I+A198D. Another preferred combination is M199I+Y219F. Another preferred combination is M199I+V324T. Another preferred combination is M199I+T369L. Another preferred combination is M199I+A346Q.

A combination of M199I and Q276A with at least one other or exactly one other selected from the group comprising: S303P, D302Y, K180P, A198D, Y219F, V324T, T369L and A346Q is also preferred.

A combination of M199I and A198D with at least one other or exactly one other selected from the group comprising: S303P, D302Y, K180P, Q276A, Y219F, V324T, T369L and A346Q is also preferred.

A combination of M199I and Y219F with at least one other or exactly one other selected from the group comprising: S303P, D302Y, K180P, Q276A, A198D, V324T, T369L and A346Q is also preferred.

A combination of M199I and V324T with at least one other or exactly one other selected from the group comprising: S303P, D302Y, K180P, Q276A, A198D, Y219F, T369L and A346Q is also preferred.

A combination of M199I and T369L with at least one other or exactly one other selected from the group comprising: S303P, D302Y, K180P, Q276A, A198D, Y219F, V324T and A346Q is also preferred.

A combination of M199I and A346Q with at least one other or exactly one other selected from the group comprising: S303P, D302Y, K180P, Q276A, A198D, Y219F, V324T and T369L is also preferred.

Another preferred combination is M199I+Q276A+A198D. In other variants this combination is additionally combined with one or several of the following: S303P, D302Y, K180P, Y219F, V324T, T369L and A346Q. M199I+Q276A+A198D+Y219F, M199I+Q276A+A198D+V324T, M199I+Q276A+A198D+T369L and/or M199I+Q276A+A198D+A346Q is preferred. Other preferred embodiments thereof are mentioned above.

Another preferred combination is M199I+Q276A+Y219F. In other variants this combination is additionally combined with one or several of the following: S303P, D302Y, K180P, A198D, V324T, T369L and A346Q. M199I+Q276A+Y219F+V324T and/or M199I+Q276A+Y219F+T369L, M199I+Q276A+Y219F+A346Q is preferred. Other preferred embodiments thereof are mentioned above.

Another preferred combination is M199I+Q276A+V324T. In other variants this combination is additionally combined with one or several of the following: S303P, D302Y, K180P, A198D, Y219F, T369L and A346Q. M199I+Q276A+V324T+T369L and/or M199I+Q276A+V324T+A346Q is preferred. Other preferred embodiments thereof are mentioned above.

Another preferred combination is M199I+Q276A+T369L. In other variants this combination is additionally combined with one or several of the following: S303P, D302Y, K180P, A198D, Y219F, V324T and A346Q. M199I+Q276A+T369L+A346Q is preferred. Other preferred embodiments thereof are mentioned above.

Another preferred combination is M199I+Q276A+A346Q. In other variants this combination is additionally combined with one or several of the following: S303P, D302Y, K180P, A198D, Y219F, V324T and T369L. Other preferred embodiments thereof are mentioned above.

Another preferred combination is M199I+A198D+Y219F. In other variants this combination is additionally combined with one or several of the following: S303P, D302Y, K180P, Q276A, V324T, T369L and A346Q. M199I+A198D+Y219F+V324T and/or M199I+A198D+Y219F+T369L, M199I+A198D+Y219F+A346Q is preferred. Other preferred embodiments thereof are mentioned above.

Another preferred combination is M199I+A198D+V324T. In other variants this combination is additionally combined with one or several of the following: S303P, D302Y, K180P, Q276A, Y219F, T369L and A346Q. M199I+A198D+V324T+T369L, M199I+A198D+V324T+A346Q is preferred. Other preferred embodiments thereof are mentioned above.

Another preferred combination is M199I+A198D+T369L. In other variants this combination is additionally combined with one or several of the following: S303P, D302Y, K180P, Q276A, Y219F, V324T and A346Q. M199I+A198D+T369L+A346Q is preferred. Other preferred embodiments thereof are mentioned above.

Another preferred combination is M199I+A198D+A346Q. In other variants this combination is additionally combined with one or several of the following: S303P, D302Y, K180P, Q276A, Y219F, V324T and T369L. Other preferred embodiments thereof are mentioned above.

Another preferred combination is M199I+Y219F+V324T. In other variants this combination is additionally combined with one or several of the following: S303P, D302Y, K180P, Q276A, A198D, T369L and A346Q. M199I+Y219F+V324T+T369L and/or M199I+Y219F+V324T+A346Q is preferred. Other preferred embodiments thereof are mentioned above.

Another preferred combination is M199I+Y219F+T369L. In other variants this combination is additionally combined with one or several of the following: S303P, D302Y, K180P, Q276A, A198D, V324T and A346Q. M199I+Y219F+T369L+A346Q is preferred. Other preferred embodiments thereof are mentioned above.

Another preferred combination is M199I+Y219F+A346Q. In other variants this combination is additionally combined with one or several of the following: S303P, D302Y, K180P, Q276A, A198D, V324T and T369L. Other preferred embodiments thereof are mentioned above.

Another preferred combination is M199I+V324T+T369L. In other variants this combination is additionally combined with one or several of the following: S303P, D302Y, K180P, Q276A, A198D, Y219F and A346Q. M199I+V324T+T369L+A346Q is preferred. Other preferred embodiments thereof are mentioned above.

Another preferred combination is M199I+V324T+A346Q. In other variants this combination is additionally combined with one or several of the following: S303P, D302Y, K180P, Q276A, A198D, Y219F and T369L. Other preferred embodiments thereof are mentioned above.

Another preferred combination is M199I+T369L+A346Q. In other variants this combination is additionally combined with one or several of the following: S303P, D302Y, K180P, Q276A, A198D, Y219F and V324T. Other preferred embodiments thereof are mentioned above.

A combination of Q276A with at least one other or exactly one other selected from the group comprising: S303P, D302Y, K180P, M199I, A198D, Y219F, V324T, T369L and A346Q is preferred. Another preferred combination is Q276A+A198D. Another preferred combination is Q276A+Y219F. Another preferred combination is Q276A+V324T. Another preferred combination is Q276A+T369L. Another preferred combination is Q276A+A346Q.

A combination of Q276A and A198D with at least one other or exactly one other selected from the group comprising: S303P, D302Y, K180P, M199I, Y219F, V324T, T369L and A346Q is also preferred.

A combination of Q276A and Y219F with at least one other or exactly one other selected from the group comprising: S303P, D302Y, K180P, M199I, A198D, V324T, T369L and A346Q is also preferred.

A combination of Q276A and V324T with at least one other or exactly one other selected from the group comprising: S303P, D302Y, K180P, M199I, A198D, Y219F, T369L and A346Q is also preferred.

A combination of Q276A and T369L with at least one other or exactly one other selected from the group comprising: S303P, D302Y, K180P, M199I, A198D, Y219F, V324T and A346Q is also preferred.

A combination of Q276A and A346Q with at least one other or exactly one other selected from the group comprising: S303P, D302Y, K180P, M199I, A198D, Y219F, V324T and T369L is also preferred.

A combination of Q276A with [sic] with at least one other or exactly one other selected from the group comprising: S303P, D302Y, K180P, M199I, A198D, Y219F, V324T, T369L and A346Q is also preferred.

Another preferred combination is Q276A+A198D+Y219F. In other variants this combination is additionally combined with one or several of the following: S303P, D302Y, K180P, M199I, V324T, T369L and A346Q. Q276A+A198D+Y219F+V324T and/or Q276A+A198D+Y219F+T369L, Q276A+A198D+Y219F+A346Q is preferred. Other preferred embodiments thereof are mentioned above.

Another preferred combination is Q276A+A198D+V324T. In other variants this combination is additionally combined with one or several of the following: S303P, D302Y, K180P, M199I, Y219F, T369L and A346Q. Q276A+A198D+V324T+T369L and/or Q276A+A198D+V324T+A346Q is preferred. Other preferred embodiments thereof are mentioned above.

Another preferred combination is Q276A+A198D+T369L. In other variants this combination is additionally combined with one or several of the following: S303P, D302Y, K180P, M199I, Y219F, V324T and A346Q. Q276A+A198D+T369L+A346Q is preferred. Other preferred embodiments thereof are mentioned above.

Another preferred combination is Q276A+A198D+A346Q. In other variants this combination is additionally combined with one or several of the following: S303P, D302Y, K180P, M199I, Y219F, V324T and T369L. Other preferred embodiments thereof are mentioned above.

Another preferred combination is Q276A+Y219F+V324T. In other variants this combination is additionally combined with one or several of the following: S303P, D302Y, K180P, M199I, A198D, T369L and A346Q. Q276A+Y219F+V324T+T369L and/or Q276A+Y219F+V324T+A346Q is preferred. Other preferred embodiments thereof are mentioned above.

Another preferred combination is Q276A+Y219F+T369L. In other variants this combination is additionally combined with one or several of the following: S303P, D302Y, K180P, M199I, A198D, V324T and A346Q. Q276A+Y219F+T369L+A346Q is preferred. Other preferred embodiments thereof are mentioned above.

Another preferred combination is Q276A+Y219F+A346Q. In other variants this combination is additionally combined with one or several of the following: S303P, D302Y, K180P, M199I, A198D, V324T and T369L. Other preferred embodiments thereof are mentioned above.

Another preferred combination is Q276A+V324T+T369L. In other variants this combination is additionally combined with one or several of the following: S303P, D302Y, K180P, M199I, A198D, Y219F and A346Q. Q276A+V324T+T369L+A346Q is preferred. Other preferred embodiments thereof are mentioned above.

Another preferred combination is Q276A+V324T+A346Q. In other variants this combination is additionally combined with one or several of the following: S303P, D302Y, K180P, M199I, A198D, Y219F and T369L. Other preferred embodiments thereof are mentioned above.

Another preferred combination is Q276A+T369L+A346Q. In other variants this combination is additionally combined with one or several of the following: S303P, D302Y, K180P, M199I, A198D, Y219F and V324T. Other preferred embodiments thereof are mentioned above.

A combination of A198D with at least one other or exactly one other selected from the group comprising: S303P, D302Y, K180P, M199I, Q276A, Y219F, V324T, T369L and A346Q is preferred. One preferred combination is A198D+Y219F. Another preferred combination is A198D+V324T. Another preferred combination is A198D+T369L. Another preferred combination is A198D+A346Q.

A combination of A198D and Y219F with at least one other or exactly one other selected from the group comprising: S303P, D302Y, K180P, M199I, Q276A, V324T, T369L and A346Q is also preferred.

A combination of A198D and V324T with at least one other or exactly one other selected from the group comprising: S303P, D302Y, K180P, M199I, Q276A, Y219F, T369L and A346Q is also preferred.

A combination of A198D and T369L with at least one other or exactly one other selected from the group comprising: S303P, D302Y, K180P, M199I, Q276A, Y219F, V324T and A346Q is also preferred.

A combination of A198D and A346Q with at least one other or exactly one other selected from the group comprising: S303P, D302Y, K180P, M199I, Q276A, Y219F, V324T and T369L is also preferred.

A combination of A198D with [sic] with at least one other or exactly one other selected from the group comprising: S303P, D302Y, K180P, M199I, Q276A, Y219F, V324T, T369L and A346Q is also preferred.

One preferred combination is A198D+Y219F+V324T. In other variants this combination is additionally combined with one or several of the following: S303P, D302Y, K180P, M199I, Q276A, T369L and A346Q. A198D+Y219F+V324T+T369L and/or A198D+Y219F+V324T+A346Q is preferred. Other preferred embodiments thereof are mentioned above.

Another preferred combination is A198D+Y219F+T369L. In other variants this combination is additionally combined with one or several of the following: S303P, D302Y, K180P, M199I, Q276A, V324T and A346Q. A198D+Y219F+T369L+A346Q is preferred. Other preferred embodiments thereof are mentioned above.

Another preferred combination is A198D+Y219F+A346Q. In other variants this combination is additionally combined with one or several of the following: S303P, D302Y, K180P, M199I, Q276A, V324T and T369L. Other preferred embodiments thereof are mentioned above.

Another preferred combination is A198D+V324T+T369L. In other variants this combination is additionally combined with one or several of the following: S303P, D302Y, K180P, M199I, Q276A, Y219F and A346Q. A198D+V324T+T369L+A346Q is preferred. Other preferred embodiments thereof are mentioned above.

Another preferred combination is A198D+V324T+A346Q. In other variants this combination is additionally combined with one or several of the following: S303P, D302Y, K180P, M199I, Q276A, Y219F and T369L. Other preferred embodiments thereof are mentioned above.

Another preferred combination is A198D+T369L+A346Q. In other variants this combination is additionally combined with one or several of the following: S303P, D302Y, K180P, M199I, Q276A, Y219F and V324T. Other preferred embodiments thereof are mentioned above.

A combination of Y219F with at least one other or exactly one other selected from the group comprising: S303P, D302Y, K180P, M199I, Q276A, A198D, V324T, T369L and A346Q is preferred. One preferred combination is Y219F+V324T. Another preferred combination is Y219F+T369L. Another preferred combination is Y219F+A346Q.

A combination of Y219F and V324T with at least one other or exactly one other selected from the group comprising: S303P, D302Y, K180P, M199I, Q276A, A198D, T369L and A346Q is also preferred.

A combination of Y219F and T369L with at least one other or exactly one other selected from the group comprising: S303P, D302Y, K180P, M199I, Q276A, A198D, V324T and A346Q is also preferred.

A combination of Y219F and A346Q with at least one other or exactly one other selected from the group comprising: S303P, D302Y, K180P, M199I, Q276A, A198D, V324T and T369L is also preferred.

A combination of Y219F with [sic] with at least one other or exactly one other selected from the group comprising: S303P, D302Y, K180P, M199I, Q276A, A198D, V324T, T369L and A346Q is also preferred.

Another preferred combination is Y219F+V324T+T369L. In other variants this combination is additionally combined with one or several of the following: S303P, D302Y, K180P, M199I, Q276A, A198D and A346Q. Y219F+V324T+T369L+A346Q is preferred. Other preferred embodiments thereof are mentioned above.

Another preferred combination is Y219F+V324T+A346Q. In other variants this combination is additionally combined with one or several of the following: S303P, D302Y, K180P, M199I, Q276A, A198D and T369L. Other preferred embodiments thereof are mentioned above.

Another preferred combination is Y219F+T369L+A346Q. In other variants this combination is additionally combined with one or several of the following: S303P, D302Y, K180P, M199I, Q276A, A198D and V324T. Other preferred embodiments thereof are mentioned above.

A combination of V324T is preferred with at least one other or exactly one other selected from the group comprising: S303P, D302Y, K180P, M199I, Q276A, A198D, Y219F, T369L and A346Q. One preferred combination is V324T+T369L. Another preferred combination is V324T+A346Q.

A combination of V324T and T369L with at least one other or exactly one other selected from the group comprising: S303P, D302Y, K180P, M199I, Q276A, A198D, Y219F and A346Q is also preferred.

A combination of V324T and A346Q with at least one other or exactly one other selected from the group comprising: S303P, D302Y, K180P, M199I, Q276A, A198D, Y219F and T369L is also preferred.

One preferred combination is V324T+T369L+A346Q. In other variants this combination is additionally combined with one or several of the following: S303P, D302Y, K180P, M199I, Q276A, A198D and Y219F. Other preferred embodiments thereof are mentioned above.

A combination of T369L with at least one other or exactly one other selected from the group comprising: S303P, D302Y, K180P, M199I, Q276A, A198D, Y219F, V324T and A346Q is preferred. One preferred combination is T369L+A346Q.

A combination of T369L and A346Q with at least one other or exactly one other selected from the group comprising: S303P, D302Y, K180P, M199I, Q276A, A198D, Y219F and V324T is also preferred.

The invention also relates to nucleic acid molecules, i.e., polynucleotide molecules, that each respectively encode the above-mentioned SmuA amino acid sequences modified through amino acid substitution. This includes many polynucleotide molecules, of course, which because of the degenerative genetic code can be found in several embodiments, but encode the same polyamino acid molecules according to the invention. The expert is familiar with bioinformatic methods that can be used to ascertain the defined group of polynucleotide molecules which encode the amino acid sequence, from any given amino acid sequence of the invention.

In a first embodiment the polynucleotide molecule according to the invention is present as an isolated polynucleic acid molecule.

In an alternative embodiment the polynucleotide molecule according to the invention is present in the form of, or as a component of, a construct which mediates the expression of the modified sucrose mutase of the invention in a biological system, particularly in a biological cell, preferably in a bacteria cell.

One such construct is, [in] a first embodiment, an expression cassette which contains one or several copies of the polynucleotide molecule of the invention. Preferably, the expression cassette also contains at least one promoter element for regulating the expression of the polynucleotide molecule and, if necessary, a terminator sequence as well.

Another object of the invention is a vector construct containing at least one or preferably several of the expression cassettes.

Possible promoters of the expression cassette and vector construct are the well-known promoters for the expression of the polynucleotide molecule of the invention in a biological system. The native promoter of the wild-type sucrose mutase gene is preferred. Alternatively preferred is a promoter element that better mediates the expression of the sucrose mutase modified according to the invention, in particular a greatly enhanced activity, i.e., especially the volume activity of the expressed sucrose mutase.

In addition to the aforementioned expression vector for preferably extrachromosomal expression of the modified sucrose mutase of the invention, the invention also relates to a construct that can be used to substitute a sucrose mutase-encoding wild-type gene contained in the genome of a biological cell, for the polynucleotide molecule of the invention, encoding the modified sucrose mutase according to the invention. Such a substitute plasmid is used to integrate the polynucleotide molecule of the invention in the chromosomal genome of the cell. The gene substitution-mediating substitute plasmid is specifically designed not to replicate itself in the host cell into which it is introduced. A preferred vector construct is a pUT derivative that is based on an R6K replication origin. This vector specifically does not replicate itself in host cells of the strain *P. rubrum*, at least not conditionally.

The polynucleotide molecule of the invention can be inserted into a host cell either in the form of an extrachromosomal expression construct or by means of chromosomal gene substitution; such host cell is selected from host cells that can otherwise be used to transform saccharose into isomaltulose.

The invention also relates to the use of the above-characterized polynucleotide molecules, substitution promoters and their fragments or complete sucrose mutase expression cassettes according to the invention, for producing a cell according to the invention.

The invention also relates to the use of the above-characterized vector, according to the first aspect of the invention thus a substitute plasmid, according to the second aspect of the invention thus an expression vector, for the production of such a cell.

The invention also includes biological cells with a novel product spectrum, specifically cells able to synthesize an isomaltulose composition from a substrate containing saccharose that features at least 85% by weight or more (relative to the dry substance weight of the isomaltulose composition), preferably 86% by weight or more, 87% by weight or more, 88% by weight or more, 89% by weight or more, 90% by weight or more, 91% by weight or more, 92% by weight or more, 93% by weight or more, 94% by weight or more, especially preferably 95% by weight or more.

A host cell is preferred that is selected [sic] from microorganisms of the groups gammaproteobacteria and unclassified gammaproteobacteria. The cell is preferably selected from the group comprising microorganisms of the types: *Escherichia, Salmonella, Serratia, Erwinia, Enterobacter, Klebsiella, Rauoltella, Pectobacterium, Pseudomonas, Azotobacter, Pantoea, Leucanea* and *Protaminobacter*. The cell is especially preferably selected from the group comprising: *Klebsiella* sp., especially strain LX3 and strain NK33-98-8, *Klebsiella pneumoniae*, especially strain 342; *Enterobacter* sp., especially strain SZ62; *Enterobacter* sp., especially strain FMB1; *Rauoltella planticola; Pantoea dispersa; Erwinia rhapontici; Erwinia tasmaniensis*, especially strain Et1/99; *Pectobacterium atrosepticum*, especially strain SCRI 1043; *Pectobacterium carovotum*, especially subspecies *brasiliensis*, especially strain PBR 1692; *Protaminobacter rubrum; Pseudomonas mesoacidophila; Serratia plymuthica* as well as *Azotobacter vinelandii* and *Leucanea leucocephalia*. In an especially preferred variant the cell is *Protaminobacter rubrum* (*P. rubrum*) or a biotechnologically usable strain derived from it. The invention also covers immobilized and/or otherwise modified forms of such host cells, which can be especially suited for use in biotechnological methods.

In particular the host cells are deletion mutants for a wild-type sucrose mutase gene possibly present in the cell.

A preferred variant is a cell in which the chromosomal sucrose mutase wild-type gene present in the cell is substituted for a nucleotide sequence in the chromosome that encodes the sucrose mutase enzyme modified according to the invention. In a first variant this modified gene of the invention is subject to the control of the promoter of the wild-type sucrose mutase gene. In another preferred variant this modified gene of the invention is under the control of a preferably endogenic homologous substitution promoter. Such a promoter is selected especially from the group comprising: the promoter of the gene of the 3,4-Dihydroxy-2-butanone-4-phosphate synthase ribB, the promoter of the gene that encodes the [old] membrane protein ompA, the promoter of the gene that encodes the putative transcription activator ECA2934, the promoter of the gene of the ribonuclease E me, the promoter of the operon of the 50S-ribosomal L21-protein, the promoter of the operon of the cold shock protein CspE, the promoter of the operon of the 50S-ribosomal L28-protein and the promoter of the gene of the NAD-dependent epimerase-dehydratase and functional promoter fragments thereof that have the capability to control the expression of the modified sucrose mutase modified of the invention. Reference is made to the entire content of disclosure DE 10 2009 053566, particularly tables 1A, 1B and sequences SEQ ID No.: 2 through 21 of the sequence protocol.

The invention also relates to cells in which the modified sucrose mutase of the invention is expressed extrachromosomally (episomally), particularly under the control of at least one of the above-characterized promoters.

The invention also relates to means for producing such cells. One such means is the polynucleotide molecule that contains at least one or more copies of an expressible segment that encodes the modified sucrose mutase of the invention, and additionally at least one or more copies of another element that regulates the expression of such sucrose mutase, i.e., especially a promoter element. In an alternative variant of this aspect of the invention, the polynucleotide molecule of the invention is present in isolated form as an expression cassette. It can therefore be transferred, e.g., into a host cell in an established manner. Another object of the invention is a method for producing a cell according to the invention that is capable of transforming saccharose into isomaltulose or compositions containing isomaltulose, whereby the method at least contains the following steps: In a first step, a wild-type strain or an already classically or recombinantly modified strain of the cell is provided; in a second step this strain is brought into contact with or linked to at least one of the above-characterized polynucleotide molecules of the invention, encoding the modified sucrose mutase of the invention, and/or at least one of the above-characterized vectors, such that the polynucleotide molecule of the invention is introduced into the cell in an expressible form.

In relation to the invention, an "isomaltulose composition" is understood to mean the isomerization product [produced] through [the] activity of the sucrose mutase from the saccharose substrate. Its by far predominant constituent is isomaltulose. Other components are, in particular, trehalulose, isomelicitose and fructose and glucose. It is understood to mean the following composition in particular: 80 to 99% isomaltulose, 1 to 10% trehalulose, 0 to 0.5% isomelicitose, 0 to 0.2% trisaccharide, 0 to 5% monosaccharide and 0 to 0.2% residual saccharide.

The amount of isomaltulose in the isomaltulose composition is especially preferably at least 85% by weight or more (relative to the dry substance weight of the isomaltulose composition), preferably 86% by weight or more, 87% by weight or more, 88% by weight or more, 89% by weight or more, 90% by weight or more, 91% by weight or more, 92% by weight or more, 93% by weight or more, 94% by weight or more, especially preferably 95% by weight or more. The invention also relates to methods for the biotechnological production of isomaltulose and/or a composition containing isomaltulose, from the substrate saccharose or a substrate containing saccharose.

In a first aspect it is a method for the biotechnological production of isomaltulose or an isomaltulose composition from a substrate containing saccharose, in which, in a first step, a substrate containing saccharose is brought into contact with the sucrose mutase of the invention or with the biocatalyst, specifically under conditions which facilitate a transformation of the substrate into isomaltulose or an isomaltulose composition.

In another aspect it is a method for the biotechnological production of isomaltulose or an isomaltulose composition, from a substrate containing saccharose, in which, in a first step containing the step: the above-characterized cell is cultivated in a culture medium containing the substrate under conditions which facilitate a transformation of the substrate into isomaltulose or an isomaltulose composition. In a preferred subsequent step the isomaltulose or the isomaltulose composition is preferably isolated from the culture medium. In one particular embodiment of the cell-based production, the cells are immobilized on or in a matrix, particularly an alginate matrix or the like, in a well-known manner. This is particularly intended for the large-scale transformation of saccharose into isomaltulose or the isomaltulose composition.

An object of the invention is therefore also the use of an above-characterized cell of the invention for the biotechnological production of isomaltulose or an isomaltulose composition, preferably from saccharose or a substrate containing saccharose, and preferably according to the method described here.

It is also intended for the polynucleotide molecule of the invention to be used particularly in an isolated form or as a component of a cell fragment, for developing cell-free systems and biocatalysts. In one preferred embodiment the biocatalyst features a support on which the sucrose mutase modified according to the invention is immobilized. In another preferred embodiment the polynucleotide molecule of the invention, particularly in isolated form, is used not immobilized as a sucrose mutase biocatalyst, particularly in soluble form.

The invention therefore also relates to biocatalysts that are basically cell-free and preferably characterized in that the modified sucrose mutase according to the invention is present immobilized on them. A preferred first variant are cell fragments immobilized on a support, preferably a filter membrane. Alternatively, an isolated polyamino acid molecule according to the invention, preferably produced synthetically in a well-known manner, is present that exhibits the modified sucrose mutase activity of the invention. In an alternative preferred embodiment the biocatalyst is formed by the non-immobilized, isolated polynucleotide molecule of the invention with sucrose mutase activity.

The invention is explained in more detail through the following examples, which are not to be understood as limitative.

The sequence protocol contains:

SEQ ID NO.: 1 amino acid sequence of the wild-type sucrose mutase SmuA from *P. rubrum* according to Ravaud et al. 2009 (FEBS Letters 583, 1964-1968):

```
TQQPLLNEKSIEQSKTIPKWWKEAVFYQVYPRSFKDTNGDGIGDINGIIEKLDYLKALGI

DAIWINPHYDSPNTDNGYDIRDYRKIMKEYGTMEDFDRLISEMKKRNMRLMIDVVINHTS

DQNEWFVKSKSSKDNPYRGYYFWKDAKEGQAPNNYPSFFGGSAWQKDEKTNQYYLHYFAK

QQPDLNWDNPKVRQDLYAMLRFWLDKGVSGLRFDTVATYSKIPDFPNLTQQQLKNFAAEY

TKGPNIHRYVNEMNKEVLSHYDIATAGEIFGVPLDQSIKFFDRRRDELNIAFTFDLIRLD

RDSDQRWRRKDWKLSQFRQIIDNVDRTAGEYGWNAFFLDNHDNPRAVSHFGDDRPQWREP

SAKALATLTLTQRATPFIYQGSELGMTNYPFKAIDEFDDIEVKGFWHDYVETGKVKADEF

LQNVRLTSRDNSRTPFQWDGSKNAGFTSGKPWFKVNPNYQEINAVSQVTQPDSVFNYYRQ

LIKIRHDIPALTYGTYTDLDPANDSVYAYTRSLGAEKYLVVVNFKEQMMRYKLPDNLSIE

KVIIDSNSKNVVKKNDSLLELKPWQSGVYKLNQ
```

SEQ ID NO.:2 DNA sequence of the 1942 bp XmaI/PstI fragment, which after cloning results in a non-replicative vector, e.g., the smuA-deletion plasmid pUT-GntR-P3C1-DSmuA (FIG. 1) and can be used for the deletion of the smuA-gene through homologous recombination. The DNA sequence results from a fusion of two DNA fragments that are located in *P. rubrum* 3C1 upstream and downstream from the smuA gene to be deleted.

```
CCCGGGATCGCATTCATGTTTTCTCCTTCGGTGAAGTGGTCTACTTTTATGGCGATTTGT

ATACATTAAAGTGATCAAGGAAAAAATAGCCAGAGGAATAGCCAAATAAATTTCAGGTTT

TACAGTGCGGTAACCTCTTTTTGTTGCGCGGTTATCAGGATTCATTTAGGGATAAAGAGG

TCTTCAAGTGATCTACAAAACGCTTGCTGAACGTCTGAGAATACGTATCAATTCTGCTGA

TTTTGCTATCGGCGATGCTTTACCCAGTGAGAAACGTCTGGCTGCCGAATTTTCTGTATC

GAGGATGACACTCCGCAAAGCGGTAAATTTACTGATTGAATGGGGCTGGTACGTCGCTG

TCACGGCAGCGGAACCTTCGTCGCGCAGAAAGATCTCCAACATGAAACTCGTGGGCTGAT

GGGGTTTTCAGAACTGATGAAAGAACTGGGCCGCCCCACGGTGAGCGAGGTGCTGGAGTT

TCGAATGATGGGAGCCCCCCAGCCATCGCCAGCCAGCTGCGAATCAAGGCCGATGAACG

CATTTACTATTCGCGTCGCGTAAGGTTTGTGGAAGGGAAGCCTGTGGTGCTGGAAGATAG

TTACATGCCTGGCAGGTTATTTGGCAACCTTTCAGTCGCACATCTGGAGGGTTCAAAGTT

TTCGTATATAGAAGACGAATGCCATATCAATATCGCAGGGAATTACGAAAGCTTCAGCCC

GATCTTGGCAGACAGCACGATCGGCGCGCTACTGCACGTTGCCGAAGGCACGCCGCTGCT

GCGCCTGACATCGCTTTCTTACAGTGATACCGGCGACTATATCAACTATTCGGTGATATT
```

-continued

```
CAGAAATGCCAATGAATACCACGTGGACTACCATTTGAAGAGGAATAAATAGCGGGCGAA

GGGGAGCTACATTCCTACTATATAGCAATTCTGTTGCCTAGTGTAATGCGAGTTGCCCGC

CGGATAAACCAATAACCGCATTCTCCGCAGGGGGCCGAATTGTGCTTTTGCCAATTGCCC

TGATTAATCATTAGCGTTATAGTCAGAATGCTTATTCTCAGGGCGGGGTGCAAGTCCCCA

CCGGCGGTAAATCACCTTCTACGGTGAAAGCCCGCGAGCGCTCAGCCAGTCTCTTGTAGT

TTGGTTAGAGGTCAGCAGATCCGGTGTAATTCCGGGGCCGACGGTTATAGTCCGGATGGG

AGAGAGTAACGGTATCTGCCGGGCTTGCGCCCGCTTGCGTTATTTTTTAGAAACAGGAG

AGTATTGTAATGCATTTTGTTTAAACTAAATCAATAAATCTCATAGTCACGCCAAATAAT

GTAAATATATTGAAACTATTAAAACCGGCATTTTATGCCGGTTTTTTTAGCGCAAAATAG

GGCTGGCAAAGATAAAGCAGGAGGCTACCACCGTGAGCTATATGCTTTTTTAAAAGGCAA

GATTCTCCATCGAGGCTCTGCCGTCACCCGAACGCGATAAACCGCGTTTATCCTCAGATG

CCTGGCCGTTGCGCGCAAACGAAGACCGGGGTTTGAGGGCTTGTGGGGCAACGCCGGCGA

GCCAGTCAGCTTCTCGTGGGTGCGAGCACATTGCTAATGAACAATCTCGCTTCAAATGTT

ATCGTGAGAATGAAGTGTTGCAGTGGCGCCGCCGGGGTTTGCGCTCGATTCAGGTCTGAT

TCACATAACAAGGTCACATGGAAATGAAAGTGTTATTCATCGCTTCGCTAGGCGCTTTAT

CGTTAATGCAAGCATCATTCTCCTTCGCGGATAATGCCAATGGGAAAAACATCTATTCAC

AGAGATGTACTATGTGCCACGGAACCGATCTCAAAGGCACGGGCCATTGGCTGATAAAA

CCAACCCGCCGACACCTGATCTGACAACCCCCGCTTTCAAAGCACGCCTCAATGATTATC

CGGGCGTTATTGTATCCTGCAG
```

SEQ ID No.: 3 nucleotide sequence of the full length gene that codes for the SmuA amino acid substitution variant D302Y. Substituted nucleotides are bolded.

```
ATGCCCCGTCAAGGATTGAAAACTGCACTAGCGATTTTTCTAACCACATCATTATGCATC

TCATGCCAGCAAGCCTTCGGTACGCAACAACCCTTGCTTAACGAAAAGAGTATCGAACAG

TCGAAAACCATACCTAAATGGTGGAAGGAGGCTGTTTTTTATCAGGTGTATCCGCGCTCC

TTTAAAGACACCAACGGAGATGGCATCGGGGATATTAACGGCATCATAGAAAAATTAGAC

TATCTAAAAGCCTTGGGGATTGATGCCATTTGGATCAACCCACATTATGATTCTCCGAAC

ACGGATAATGGTTACGATATACGTGATTATCGAAAAATCATGAAAGAATATGGCACGATG

GAGGATTTTGACCGCCTGATTTCTGAAATGAAAAAACGGAATATGCGGTTGATGATTGAT

GTGGTCATCAACCACACCAGCGATCAAAACGAATGGTTTGTTAAAAGTAAAAGCAGTAAG

GATAATCCTTATCGCGGCTATTATTTCTGGAAAGATGCTAAAGAAGGGCAGGCGCCTAAT

AATTACCCTTCATTCTTTGGTGGCTCGGCGTGGCAAAAAGATGAAAAGACCAATCAATAC

TACCTGCACTATTTTGCTAAACAACAGCCTGACCTAAACTGGGATAATCCCAAAGTCCGT

CAAGATCTTTATGCAATGTTACGTTTCTGGTTAGATAAAGGCGTGTCTGGTTTACGTTTT

GATACGGTAGCGACCTACTCAAAAATTCCGGATTTCCCAAATCTCACCCAACAACAGCTG

AAGAATTTTGCAGCGGAGTATACCAAGGGCCCTAATATTCATCGTTACGTCAATGAAATG

AATAAAGAGGTCTTGTCTCATTACGACATTGCGACTGCCGGTGAAATCTTTGGCGTACCC

TTGGATCAATCGATAAAGTTCTTCGATCGCCGCCGTGATGAGCTGAACATTGCATTTACC

TTTGACTTAATCAGACTCGATCGATATTCTGATCAAAGATGGCGTCGAAAAGATTGGAAA

TTGTCGCAATTCCGGCAGATCATCGATAACGTTGACCGTACTGCAGGAGAATATGGTTGG
```

```
AATGCCTTCTTCTTGGATAACCACGACAATCCGCGCGCTGTCTCGCACTTTGGCGATGAT

CGCCCACAATGGCGTGAGCCATCGGCTAAAGCGCTTGCAACCTTGACGCTGACTCAACGA

GCAACACCTTTTATTTATCAAGGTTCAGAATTGGGCATGACCAATTACCCGTTTAAAGCT

ATTGATGAATTCGATGATATTGAGGTGAAAGGTTTTTGGCATGACTACGTTGAGACAGGA

AAGGTCAAAGCCGACGAGTTCTTGCAAAATGTACGCCTGACGAGCAGGGATAACAGCCGG

ACGCCGTTCCAATGGGATGGGAGCAAAAATGCAGGATTCACGAGCGGAAAACCTTGGTTC

AAGGTCAACCCAAACTACCAGGAAATCAATGCAGTAAGTCAAGTCACACAACCCGACTCA

GTATTTAACTATTATCGTCAGTTGATCAAGATAAGGCATGACATCCCGGCACTGACCTAT

GGTACATACACCGATTTGGATCCTGCAAATGATTCGGTCTACGCCTATACACGCAGCCTT

GGGGCGGAAAAATATCTTGTTGTTGTTAACTTCAAGGAGCAAATGATGAGATATAAATTA

CCGGATAATTTATCCATTGAGAAAGTGATTATAGACAGCAACAGCAAAAACGTGGTGAAA

AAGAATGATTCATTACTCGAGCTAAAACCATGGCAGTCAGGGGTTTATAAACTAAATCAA

TAA
```

SEQ ID No.: 4 nucleotide sequence of the full length gene that codes for the SmuA double mutant D302Y/S303P. Substituted nucleotides are bolded.

```
ATGCCCCGTCAAGGATTGAAAACTGCACTAGCGATTTTTCTAACCACATCATTATGCATC

TCATGCCAGCAAGCCTTCGGTACGCAACAACCCTTGCTTAACGAAAAGAGTATCGAACAG

TCGAAAACCATACCTAAATGGTGGAAGGAGGCTGTTTTTTATCAGGTGTATCCGCGCTCC

TTTAAAGACACCAACGGAGATGGCATCGGGGATATTAACGGCATCATAGAAAAATTAGAC

TATCTAAAAGCCTTGGGGATTGATGCCATTTGGATCAACCCACATTATGATTCTCCGAAC

ACGGATAATGGTTACGATATACGTGATTATCGAAAAATCATGAAAGAATATGGCACGATG

GAGGATTTTGACCGCCTGATTTCTGAAATGAAAAAACGGAATATGCGGTTGATGATTGAT

GTGGTCATCAACCACACCAGCGATCAAAACGAATGGTTTGTTAAAAGTAAAAGCAGTAAG

GATAATCCTTATCGCGGCTATTATTTCTGGAAAGATGCTAAAGAAGGGCAGGCGCCTAAT

AATTACCCTTCATTCTTTGGTGGCTCGGCGTGGCAAAAAGATGAAAAGACCAATCAATAC

TACCTGCACTATTTTGCTAAACAACAGCCTGACCTAAACTGGGATAATCCCAAAGTCCGT

CAAGATCTTTATGCAATGTTACGTTTCTGGTTAGATAAAGGCGTGTCTGGTTTACGTTTT

GATACGGTAGCGACCTACTCAAAAATTCCGGATTTCCCAAATCTCACCCAACAACAGCTG

AAGAATTTTGCAGCGGAGTATACCAAGGGCCCTAATATTCATCGTTACGTCAATGAAATG

AATAAAGAGGTCTTGTCTCATTACGACATTGCGACTGCCGGTGAAATCTTTGGCGTACCC

TTGGATCAATCGATAAAGTTCTTCGATCGCCGCCGTGATGAGCTGAACATTGCATTTACC

TTTGACTTAATCAGACTCGATCGATATCCTGATCAAAGATGGCGTCGAAAAGATTGGAAA

TTGTCGCAATTCCGGCAGATCATCGATAACGTTGACCGTACTGCAGGAGAATATGGTTGG

AATGCCTTCTTCTTGGATAACCACGACAATCCGCGCGCTGTCTCGCACTTTGGCGATGAT

CGCCCACAATGGCGTGAGCCATCGGCTAAAGCGCTTGCAACCTTGACGCTGACTCAACGA

GCAACACCTTTTATTTATCAAGGTTCAGAATTGGGCATGACCAATTACCCGTTTAAAGCT

ATTGATGAATTCGATGATATTGAGGTGAAAGGTTTTTGGCATGACTACGTTGAGACAGGA

AAGGTCAAAGCCGACGAGTTCTTGCAAAATGTACGCCTGACGAGCAGGGATAACAGCCGG

ACGCCGTTCCAATGGGATGGGAGCAAAAATGCAGGATTCACGAGCGGAAAACCTTGGTTC
```

-continued

```
AAGGTCAACCCAAACTACCAGGAAATCAATGCAGTAAGTCAAGTCACACAACCCGACTCA

GTATTTAACTATTATCGTCAGTTGATCAAGATAAGGCATGACATCCCGGCACTGACCTAT

GGTACATACACCGATTTGGATCCTGCAAATGATTCGGTCTACGCCTATACACGCAGCCTT

GGGGCGGAAAAATATCTTGTTGTTGTTAACTTCAAGGAGCAAATGATGAGATATAAATTA

CCGGATAATTTATCCATTGAGAAAGTGATTATAGACAGCAACAGCAAAAACGTGGTGAAA

AAGAATGATTCATTACTCGAGCTAAAACCATGGCAGTCAGGGGTTTATAAACTAAATCAA

TAA
```

EXAMPLE 1

Substitution of the smuA Wild-Type Gene for smuA-Sequence Variant Genes in P. rubrum 3C1/Z12A Sucrose mutase enzyme variants (SmuA*) modified according to the invention are characterized in the P. rubrum strain 3C1. In this strain the SmuA expression is significantly increased through the scar-free substitution of the native smuA-promoter for the homologous promoter of the 3,4-dihydroxy-2-butanone-4-phosphate synthase gene ribB (ribB-promoter sequence in strain 3C1, s, SEQ ID No.: 2 nucleotide position 1013-1270). To determine the sucrose mutase product specificity of SmuA*-sequence variants of the invention, the wild-type smuA gene present in the P. rubrum strain 3C1 was first deleted by means of homologous recombination. SmuA* variant-coding genes are then integrated into the smuA-deletion mutant through homologous recombination. This approach permits the expression of sequence-modified genes in the homologous system and the detailed assay of the product specificity of sequence variants of the invention without influence by wild-type SmuA activities.

1.1. Deletion of the Wild-Type smuA Gene in P. rubrum 3C1/Z12A

All cloning and DNA modifications are performed as described under Sambrook et al., 1989 (Molecular cloning: A laboratory manual, 2nd ed. Cold Spring Harbor Laboratory, Cold Spring Harbor, N.Y.). PCR sets, kits for nucleic acid isolation, detection and selection methods and the cultivation were carried out in a well-established manner, unless otherwise specified, according to the manufacturer's specifications.

The deletion of the wild-type smuA gene in P. rubrum 3C1/Z12A is done by means of homologous recombination. For this purpose two DNA fragments are precisely amplified upstream and downstream from the smuA gene and fused together by, e.g., ligase-free cloning (Geu-Flores, F. et al. 2007, Nucleic Acids Research 35 (7): e55) (see FIG. 1). Alternatively, there is the possibility to produce the desired DNA fragment by way of DNA synthesis. After ligation or synthesis an XmaI/PstI fragment (see SEQ ID No.: 2) is produced that features a 1267 bp area sequence homologous to the P. rubrum 3C1 chromosome upstream from the deleted smuA gene. This area codes, on the one hand, for an "open reading frame" (ORF) that features high homologies to GntR-type transcription regulators and carries, on the other hand, the P. rubrum homologous promoter 3C1 of the 3,4-dihydroxy-2-butanone-4-phosphate synthase gene ribB. Upstream from the deleted smuA gene the area homologous to the P. rubrum chromosome is 655 bp.

For performing the actual smuA deletion the 1942 bp XmaI/PstI fragment is cloned into a suitable gene substitution vector that does not replicate in P. rubrum. Base vectors suited for gene substitution in P. rubrum are so-called pUT-derivatives that are based on an R6K replication origin (Herrero et al., 1990, J. Bacteriol., 172:6557-67). These vectors only replicate when the π-protein coding pir gene essential for replication is present. One such strain is E. coli S17-1λpir (Herrero et al., 1990, J. Bacteriol., 172:6557-67), which is used for the construction of the respective promoter substitution plasmids. An exemplary final deletion construct (pUT-GntR-P3C1-DSmuA), which mediates the precise deletion of smuA after homologous recombination, is shown in FIG. 1.

The transfer of the smuA deletion plasmid produced after P. rubrum 3C1 is preferably realized through an intergeneric conjugation between E. coli S17-1λ,pir and P. rubrum. The pUT plasmids implemented carry an "origin of transfer" (oriT) of the RP4 plasmid and can be mobilized through the RP4 plasmid chromosomally integrated into E. coli S17-λpir after P. rubrum (Herrero et al., 1990, J. Bacteriol., 172:6557-67).

The conditions for the intergeneric conjugation were optimized as follows: The selection of potential P. rubrum 3C1 transconjugants requires a plasmid marker selectable in P. rubrum (e.g., aphII, kanamycin-resistance), and a possibility to selectively inhibit the E. coli donor. By plating onto a medium containing rifamycin (100 μg/ml), rifamycin-resistant P. rubrum 3C1 colonies are spontaneously generated (P. rubrum 3C1 Rif) that do not otherwise differ from the wild-type. The conjugation is carried out as follows:

E. coli S17-λpir donor strains that carry the smuA substitution plasmid are cultivated overnight at 37° C. in a 5 ml dYT medium (per 1 liter: 16 g Bacto Trypton, 10 g Bacto Yeast Extract and 5 g NaCl) cultivated at 37° C. with kanamycin (50 μg/ml) admixed. The recipient P. rubrum 3C1 was likewise cultivated at 30° C. overnight in 5 ml dYT with rifamycin admixed (100 μg/ml). 1 ml of the overnight culture is inoculated into Erlenmeyer flasks with 100 mL of dYT medium (see above for additives) and incubated at 30° C. (P. rubrum 3C1) or 37° C. (E. coli) and 250 rpm until an OD (600 nm) of 0.4 to 0.8. Donor and recipient are mixed at a ratio of 1:4, centrifuged, washed with 1 ml dYT and finally absorbed in 100 μl dYT medium. The suspension is pipetted onto a nitrocellulose filter (pore size 0.45 μm) that is located on a dYT plate and incubated overnight at 30° C. The cells are then washed off the filter with 1 mL dYT, diluted, plated onto selection plates (dYT+kanamycin 50 µg/ml and rifamycin 100 µg/ml) and incubated overnight at 30° C.

Through the kanamycin selection, the types of *P. rubrum* 3C1 transconjugants are obtained in which the plasmids preferably integrated into the chromosome via one of the two homologous regions (FIG. 1). The incubation on a kanamycin-free medium allows the selection of smuA deletion strains in which the integrated plasmid is disintegrated via a second crossover from the chromosome.

Figure 2:
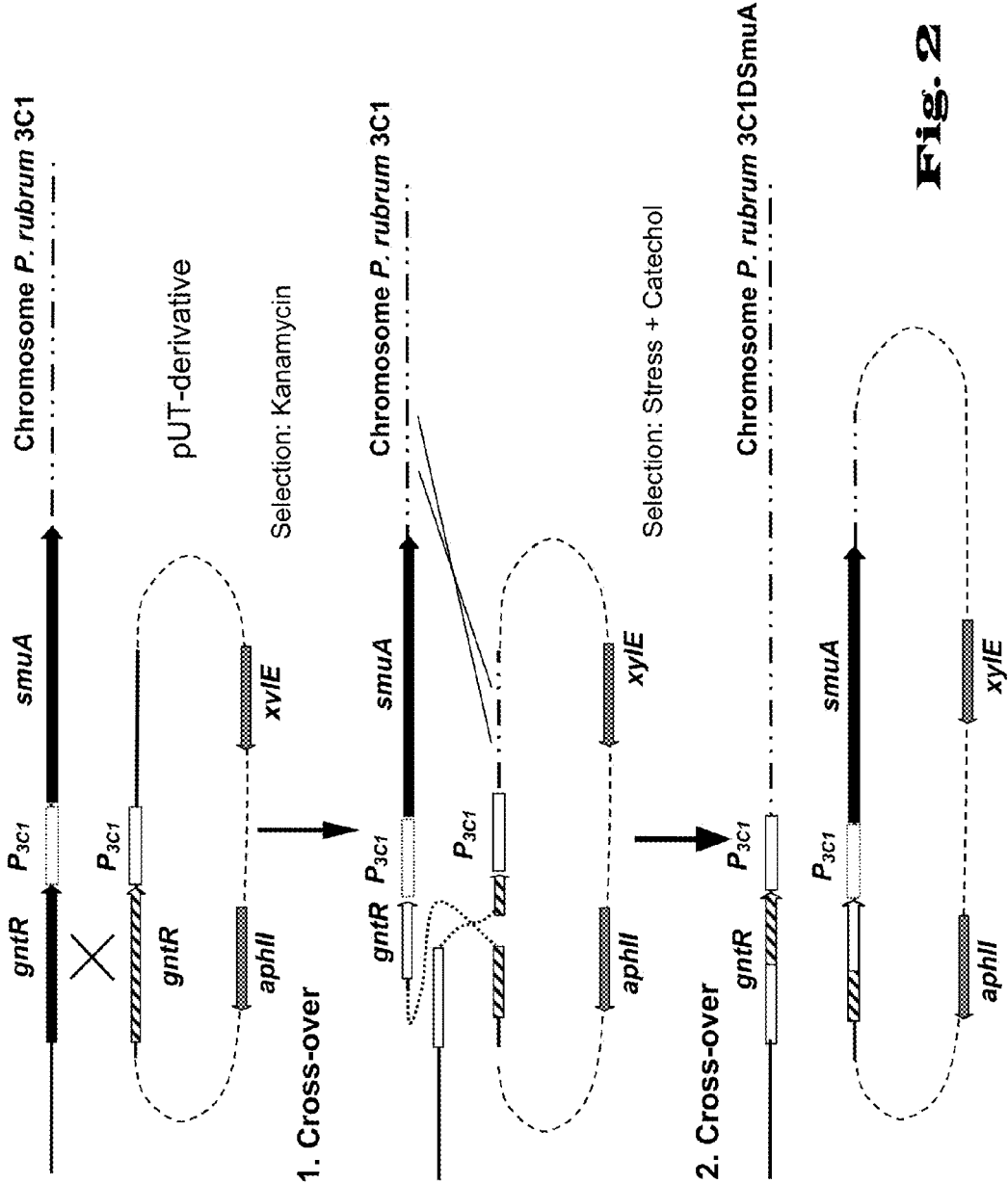
FIG. 2 illustrates schematically and by way of examples the process of the invention for producing the smuA-deletion mutant *P. rubrum* 3C1DsmuA: Substitution of the native smuA gene by homologous recombination. On the basis of a preferably non-replicative vector (e.g., pUT vector) in the host cell *P. rubrum* 3C1, an smuA-substitute plasmid is constructed preferably in *E. coli*. For this purpose two DNA fragments are amplified and fused precisely upstream and downstream from the smuA gene (see FIG. 1). After ligation, an XmaI/PstI fragment (see SEQ ID No.: 2) arises that is upstream from the deleted smuA gene and a 1267 by DNA fragment that encodes the putative gntR regulator and carries the 3C1 promoter and is flanked downstream by a 655 by DNA fragment. The plasmid created is transferred in the host cell, in this case: *P. rubrum* 3C1. Through selection preferably on kanamycin, the types of colonies are selected from it that carry the substitution plasmids in the chromosome that preferably integrated into the chromosome via at least one of the two homologous regions. The incubation on kanamycin-free medium allows the selection of deletion strains in which the integrated plasmid disintegrated out of the chromosome again via a second crossover (second recombination event). Such colonies are preferably phenotypically detectable in an established manner due to the lack of xylE activity after catechol addition (no yellow coloring). Successful production of the deletion strain can then be verified using established molecular biological methods (e.g., PCR) in order to also rule out the complete disintegration of the substitution plasmid, which leads to reconstruction of the wild-type.

To verify that disintegration was successful, a color marker gene xylE present on the substitution plasmids can be used. The xylE gene codes for a catechol-2,3 dioxygenase that transforms catechol into 2-hydroxymuconic acid-semialdehyde, which is phenotypically recognizable by a distinct yellow color. Disintegration of the previously integrated substitution plasmids is a rare event (1 in 1,000 colonies) and using the marker can be detected by the yellow color remaining in the desired clones after addition of catechol (spray reagent: 0.2 ml of a 0.5 mol/l aqueous solution). Since the disintegration of the substitution plasmid can also result in reconstitution of the wild-type, all generated smuA deletion strains can be checked and verified through PCR experiments, Southern blot analyses and genomic sequencing. The smuA deletion strain is designated by *P. rubrum* 3C1DSmuA (FIG. 2).

1.2. Production of Sequence Variants and their Integration in *P. rubrum* 3C1DSmuA Polynucleotide molecules that encode the above-mentioned SmuA amino acid sequences of the invention modified through amino acid substitution can be generated by means of a variety of methods with which the expert is familiar, such as e.g., gene synthesis, ligase-free cloning, or overlap extension PCR. The production and testing of two sequence variants, D302Y and the double mutant D302Y/S303P are described as examples (reference sequence is SEQ-ID No.: 1). SEQ-ID-No. 3 describes the nucleotide sequence of the full length gene that codes for the SmuA-amino acid substitution variant D302Y and SEQ-ID-No. 4 describes the nucleotide sequence of the full length gene that codes for the SmuA double mutant D302Y/S303P.

Figure 3:
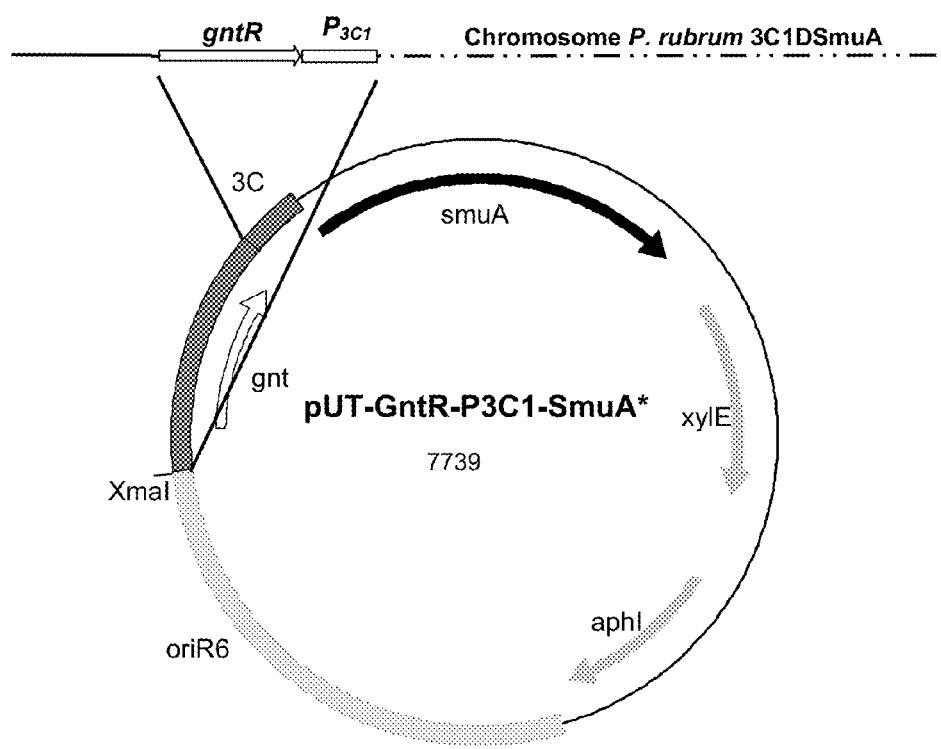
FIG. 3 illustrates schematically and by way of examples the process of the invention for the expression of smuA sequence variants in the smuA deletion mutant *P. rubrum* 3C1DsmuA: On the basis of preferably a non-replicative vector (e.g., pUT vector) in the host cell *P. rubrum* 3C1DsmuA, an integrative smuA*-expression plasmid is constructed preferably in *E. coli*. For this purpose smuA* genes that encode the aforementioned SmuA amino acid sequences according to the invention by means of amino acid substitution are fused with a 1267 by DNA fragment that encodes the putative gntR regulator and carries the 3C1 promoter required for the expression. The fusion product is then inserted into the preferably non-replicative vector (e.g., pUT vector). The plasmids created are transferred into the host cell, in this case: *P. rubrum* 3C1DSmuA. Through selection preferably on kanamycin, the types of colonies are selected whose smuA*-expression plasmids integrated into the chromosome via homologous recombination. Successful production of the integration strains can then be verified by means of established molecular biological methods (e.g., PCR). The expression of the integrated smuA*- variant genes is done through the strong 3C1 promoter.

Modified smuA gene sequence variants (smuA*), that code for amino acid substitutes of SmuA (SmuA*) according to the invention can be transferred for expression to the SmuA deletion strain described in example 1.1. For this purpose, the corresponding smuA* variant gene is precisely cloned by using methods with which the expert familiar, such as, e.g., ligase-free cloning (see above), into a non-replicative pUT derivative. As shown in FIG. 3, such a plasmid carries, like pUT-GntR-P3C1-SmuA*, in addition to the smuA variant gene smuA*, upstream from smuA*, a 1267 bp area that exhibits homologies to the chromosome of the smuA deletion strain *P. rubrum* 3C1 DSmuA. Through this area the plasmid can integrate into the chromosome of *P. rubrum* 3C1DSmuA through homologous recombination (FIG. 3). The transfer can occur through intergeneric conjugation (see example 1.1.). Through kanamycin selection those types of transconjugants are obtained in which the plasmids integrate into the chromosome via the homologous region upstream from smuA*.

Verifying that integration occurred correctly can be done through PCR experiments. Verified transconjugants carry smuA* variant genes that are constitutively expressed through the strong 3C1 promoter. The SmuA-sequence variants modified through amino acid substitution of the invention produced in these strains are then analyzed for their product spectrums in whole cell bio transformations.

EXAMPLE 2

Product Spectrum of SmuA-Variant Strains of the Invention in *P. rubrum* 3C1/Z12A 2.1 Analysis of Carbohydrate Composition by Means of HPLC The assay of separated carbohydrates is done by HPLC with the following components: HPLC pump; sampler; RI (refractory index) detector; pre-column: 10 mm×4.6 mm, amino phase (e.g., Zorbax-NH2); separation column: 250 mm×4.6 mm, amino phase (e.g., Zorbax-NH2); interface, computer and software for measurement data collection and analysis.

The measurement was carried out under the following chromatographic conditions: Injection volume: 10 µl; flow rate: 1.0 to 1.8 ml/min. The flow rate to be set for optimal separation depends on the type and condition of the separation column as well as the composition of the eluent. For other analytical parameters see Table 1.

TABLE 1

| Device: | HP1100 HPLC system | |
|---|---|---|
| Column(s): | Zorbax-NH2 250 × 4.6 mm, 5 µm with pre-column 10 × 4.6 mm | at room temperature. |
| Detector: | Refraction index detector | tempered at 30° C. |
| Eluent: | Acetonitrile 73% (v/v) | Flow: 1.400 ml/min |
| Injection volume: | 10 µL | |
| Analysis time | 30 min | |
| Sample concentration | 10% sample solution | |

2.2 Whole Cell Biotransformation in Shaking Flask

The cultivation of the strains of the invention and of wild-type control strains was done in 30 mL of LB-medium (start-$OD_{600}$ of 0.05). The cultures were each incubated at 30° C., 200 RPM in horizontal agitators. After 24 hours of fermentation, 5×OD cells are extracted, centrifuged off and washed with 1 mm calcium acetate buffer (0.01 mol/l, pH 5.5). The cell pellets (corresponding to 5×OD cells) are each resuspended in 1.25 mL calcium acetate buffer (0.01 mol/l, pH 5.5) with a saccharose solution of 0.584 mol/l (200 g/l). The batches were incubated for biotransformation in deep well plates lightly shaken at room temperature for 90 minutes. The reaction was stopped by heating treatment (5 minutes at 98° C.).

Table 2 shows the results of the HPLC analysis of the supernatants after fermentation during saccharose cultivation.

TABLE 2

| Strain/ Mutation | Isomaltulose [Standard %] | Standard Absence of | attempts [n] |
|---|---|---|---|
| D302Y/S303P | 88.4 | 0.28 | 2 |
| D302Y | 88.2 | 0.42 | 2 |
| 3C1 (control) | 87.4 | 0.30 | 11 |

The invention claimed is

1. A sucrose mutase enzyme comprising an amino acid sequence of SEQ ID NO:1, wherein the amino acid sequence has at least one amino acid substitution selected from the group consisting of S303P, D302Y, K180P, M199I, Q276A, A198D, Y219F, V324T, T369L and A346Q as compared to SEQ ID NO:1.

2. The sucrose mutase enzyme of claim 1, wherein the at least one amino acid substitution is S303P.

3. The sucrose mutase enzyme of claim 1, wherein the at least one amino acid substitution is D302Y.

4. The sucrose mutase enzyme of claim 1, wherein the at least one amino acid substitution comprises S303P and D302Y.

5. The sucrose mutase enzyme of claim 1, wherein the at least one amino acid substitution is selected from the group consisting of K180P, M199I, Q276A, A198D, Y219F, V324T, T369L and A346Q.

6. The sucrose mutase enzyme of claim 1, wherein the enzyme is an isolated polyamino acid molecule.

7. The sucrose mutase enzyme of claim 1, wherein the enzyme is immobilized on a support.

8. A nucleic acid comprising a polynucleotide molecule encoding an amino acid sequence of SEQ ID NO:1, wherein the amino acid sequence has at least one amino acid substitution selected from the group consisting of S303P, D302Y, K180P, M199I, Q276A, A198D, Y219F, V324T, T369L and A346Q as compared to SEQ ID NO:1.

9. The nucleic acid of claim 8, wherein the nucleic acid is a vector.

10. An isolated cell comprising the polynucleotide molecule of claim 8.

11. The isolated cell of claim 10, wherein the polynucleotide molecule is in the chromosome of the cell.

12. The isolated cell of claim 10, wherein the polynucleotide molecule is extrachromosomal (or episomal).

13. The isolated cell of claim 10, wherein the cell is selected from a microorganism from the group consisting of Escherichia, Salmonella, Serratia, Erwinia, Enterobacter, Klebsiella, Rauoltella, Pectobacterium, Pseudomonas, Azotobacter, Pantoea Leucanea and Protaminobacter.

14. The isolated cell of claim 13, wherein the microorganism is Protaminobacter rubrum.

15. A method of producing an isolated cell, wherein the method comprises contacting a cell with:
the polynucleotide of claim 8; or
a vector comprising the polynucleotide; or
a combination thereof.

16. A method for the biotechnological production of isomaltulose or an isomaltulose composition from a substrate containing saccharose comprising:
contacting the substrate containing the saccharose with the sucrose mutase enzyme of claim 1 under conditions that facilitate a transformation of the substrate into isomaltulose or an isomaltulose composition.

17. The method of claim 16, wherein the enzyme is produced by a cell and wherein the method comprises cultivating the cell in a culture medium containing the substrate, under conditions that facilitate a transformation of the substrate into isomaltulose or an isomaltulose composition.

18. The method of claim 17, wherein the cell is immobilized in a matrix for transformation.

19. The method of claim 17, further comprising isolation of the isomaltulose or an isomaltulose composition from the culture medium, the cell or a combination thereof.

20. The method of claim 18, further comprising isolation of the isomaltulose or an isomaltulose composition from the culture medium, the cell or a combination thereof.

* * * * *